United States Patent
Dunbar et al.

(10) Patent No.: US 11,802,265 B2
(45) Date of Patent: Oct. 31, 2023

(54) TISSUE CULTURE APPARATUS AND METHOD

(71) Applicant: Auckland Uniservices Limited, Auckland (NZ)

(72) Inventors: Peter Roderick Dunbar, Auckland (NZ); Vaughan J. Feisst, Auckland (NZ); Reece Neil Oosterbeek, Auckland (NZ); Miriam Cather Simpson, Auckland (NZ); Yuen Sze Tong, Auckland (NZ)

(73) Assignee: Auckland Uniservices LTD, Auckland (NZ)

( * ) Notice: Subject to any disclaimer, the term of this patent is extended or adjusted under 35 U.S.C. 154(b) by 542 days.

(21) Appl. No.: 15/738,570

(22) PCT Filed: Jun. 24, 2016

(86) PCT No.: PCT/NZ2016/050100
§ 371 (c)(1),
(2) Date: Dec. 20, 2017

(87) PCT Pub. No.: WO2016/209089
PCT Pub. Date: Dec. 29, 2016

(65) Prior Publication Data
US 2018/0187137 A1 Jul. 5, 2018

Related U.S. Application Data

(60) Provisional application No. 62/184,705, filed on Jun. 25, 2015.

(51) Int. Cl.
*C12M 1/04* (2006.01)
*C12M 1/12* (2006.01)
(Continued)

(52) U.S. Cl.
CPC ............ *C12M 25/14* (2013.01); *C12M 23/24* (2013.01); *C12M 23/44* (2013.01); *C12N 5/0018* (2013.01);
(Continued)

(58) Field of Classification Search
CPC ...... C12M 23/24; C12M 23/44; C12M 25/14; C08G 63/16; C08L 83/04; C12N 5/0018;
(Continued)

(56) References Cited

U.S. PATENT DOCUMENTS 4,435,508 A * 3/1984 Gabridge ............... C12M 23/42
210/445
2003/0219417 A1 11/2003 Wolfinbarger, Jr.
(Continued)

FOREIGN PATENT DOCUMENTS

| JP | 2006320304 A | 11/2006 |
| JP | 2009528856 A | 8/2009 |
| WO | 2007103865 A2 | 9/2007 |

OTHER PUBLICATIONS

Xenobiotical, 1998, vol. 28, No. 9, 815-825 (Year: 1998).*
(Continued)

*Primary Examiner* — Liban M Hassan
(74) *Attorney, Agent, or Firm* — Prismatic Law Group, PLLC; Ronald J. Kamis

(57) ABSTRACT

Described is an apparatus for culturing cells or tissue, the apparatus comprising a container comprising a bottom and at least one sidewall, wherein at least a part of the bottom comprises a gas permeable material or is adapted to engage with a gas permeable material and is perforated to allow gaseous exchange; a detachable top adapted to engage with the container to define a chamber, wherein at least a part of the top comprises a gas permeable material or is adapted to engage with a gas permeable material and is perforated to
(Continued)

allow gaseous exchange; and a scaffold adapted to receive a substrate for cells to reside upon. The apparatus is configurable between (a) a first mode in which the substrate is not disposed in gaseous communication with a gas permeable material, and (b) a second mode in which the substrate is disposed in gaseous communication with a gas permeable material.

16 Claims, 14 Drawing Sheets

(51) Int. Cl.
  *C12M 3/00* (2006.01)
  *C12N 5/00* (2006.01)
  *C12N 5/071* (2010.01)
  *C12N 5/077* (2010.01)
  *G01N 33/50* (2006.01)
  *C08G 63/16* (2006.01)
  *C08L 83/04* (2006.01)

(52) U.S. Cl.
  CPC ......... *C12N 5/0629* (2013.01); *C12N 5/0656* (2013.01); *G01N 33/5082* (2013.01); *C08G 63/16* (2013.01); *C08L 83/04* (2013.01); *C08L 2203/02* (2013.01)

(58) Field of Classification Search
  CPC . C12N 5/0656; C12N 5/0629; G01N 33/5082
  See application file for complete search history.

(56) References Cited

U.S. PATENT DOCUMENTS

| | | |
|---|---|---|
| 2004/0219659 A1 | 11/2004 | Altman et al. |
| 2006/0253192 A1* | 11/2006 | Atala ................ A61L 27/3839 623/2.13 |
| 2007/0178589 A1* | 8/2007 | Wilson ................ C12M 23/24 435/325 |
| 2008/0076170 A1* | 3/2008 | Annala ................ C12M 25/04 435/297.4 |
| 2009/0290962 A1 | 11/2009 | Fisher et al. |
| 2010/0248361 A1* | 9/2010 | Lasky ................ C12N 5/0644 435/355 |
| 2011/0136225 A1 | 6/2011 | Vunjak-Novakovic et al. |
| 2012/0210451 A1* | 8/2012 | Shimizu ................ A61P 1/18 800/8 |

OTHER PUBLICATIONS

International Search Report, International Application No. PCT/NZ2016/050100 (published as WO 2016/209089 A1), 6 pages (dated Oct. 31, 2016).

Machine Translation of JP2006320304A, pp. 1-15 (Nov. 30, 2006).

* cited by examiner (A)

(B)

(A)

(B)

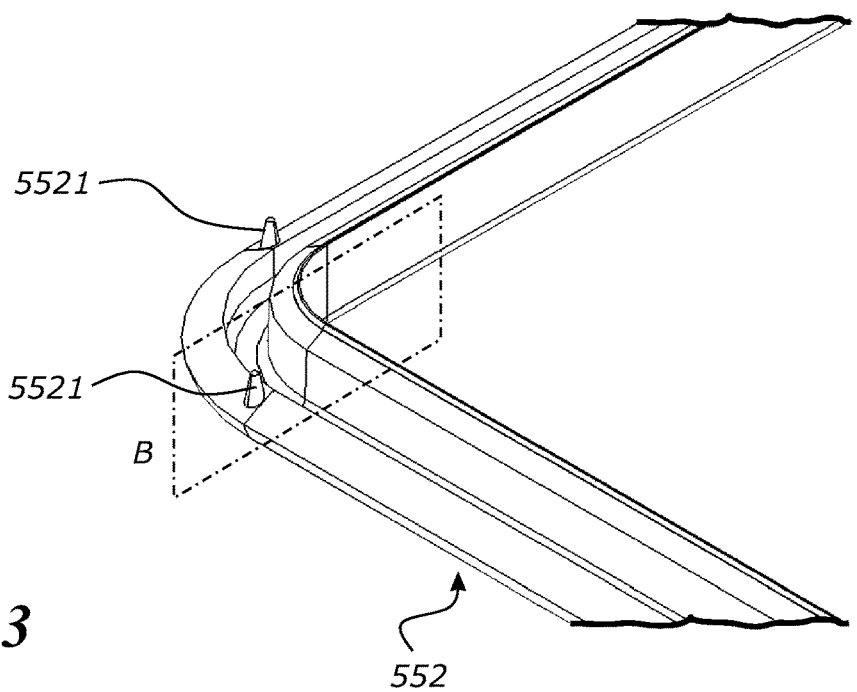
FIGURE 13
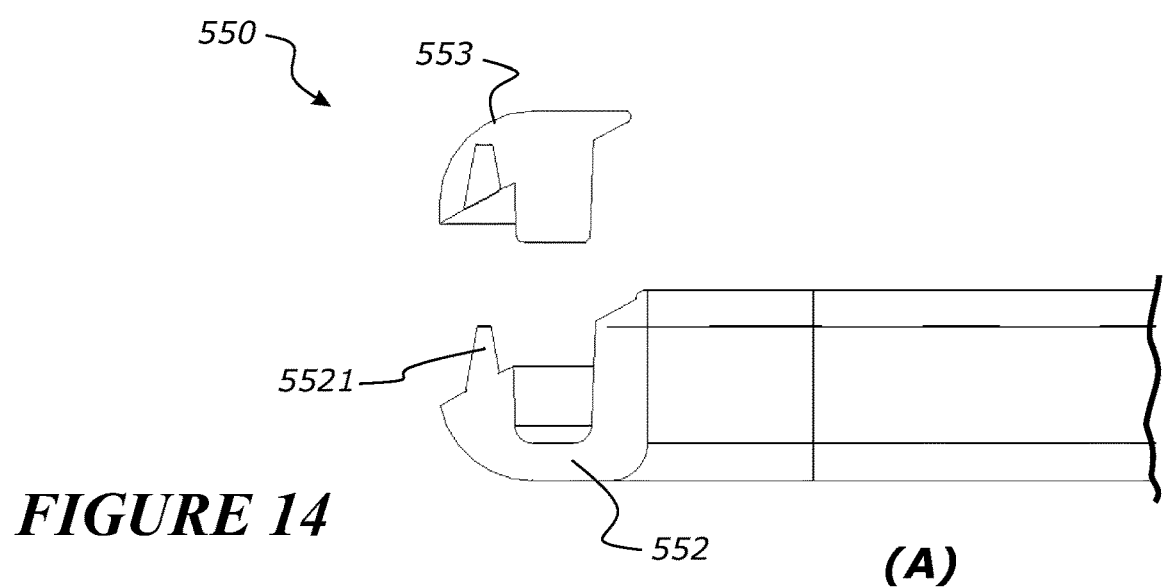
FIGURE 14
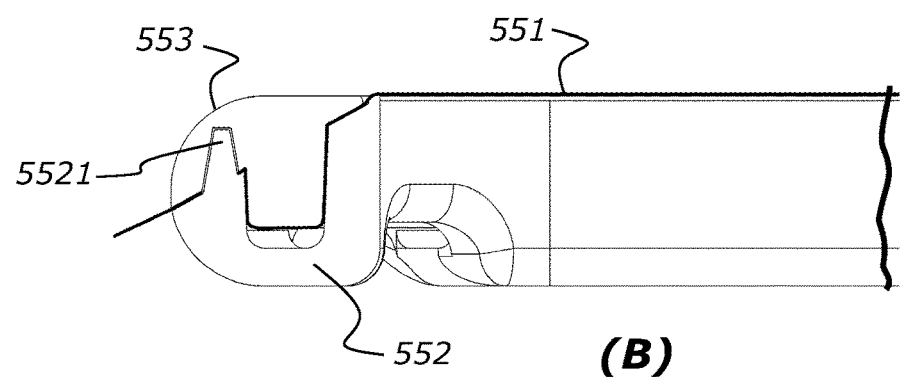

TISSUE CULTURE APPARATUS AND METHOD

CROSS-REFERENCE TO RELATED APPLICATIONS

This application is a 371 national phase of International Patent Application No. PCT/NZ2016/050100 filed Jun. 24, 2016, which claims the benefit of U.S. Provisional Application No. 62/184,705 filed Jun. 25, 2015, each of which applications is herein incorporated by reference in its entirety.

FIELD OF THE INVENTION

The present invention relates to an improved apparatus and methods for culturing cells or tissue, for example, epithelial cells or tissue comprising epithelial cells, such as skin. The invention further relates to tissue, for example, tissue comprising epithelial cells, such as full thickness skin, produced using an apparatus of the invention or by a method the invention, and the use of such tissue for treating tissue damage.

BACKGROUND TO THE INVENTION

Human and non-human animal cells or tissues engineered in vitro have a range of therapeutic and commercial applications.

For example, engineered tissues comprising epithelial cells, such as human skin may be used for autologous grafts for patients with burns or chronic wounds or the development and testing of pharmaceutical, cosmetic or other topical products.

It is highly desirable for engineered cells or tissues to have a structure and/or function similar to, or substantially the same as, the corresponding in vivo cell or tissue. However, it is very challenging to replicate the highly specific and closely regulated conditions under which the growth and differentiation of cells and the development of complex tissues occurs in vivo.

For many cells and tissues, culture at an air-liquid interface provides a high oxygen environment that promotes cell proliferation and multi-layer cell or tissue growth. Some cells or tissues must contact an air-liquid interface in order to grow or differentiate. For example, keratinocytes in the skin require contact with an air-liquid interface in order to stimulate differentiation and to induce epidermal stratification. This differentiation and growth is critical to the engineering of full thickness human skin.

There remains a need for methods and/or apparatus that provide for the culture and/or engineering of human and nonhuman animal cells or tissues in vitro under high oxygen conditions and/or conditions that mimic those present in vivo.

It is an object of the present invention to provide a method and/or apparatus that meets this need, or to at least provide the public with a useful choice.

SUMMARY OF THE INVENTION

In one aspect the invention relates to an apparatus for culturing cells or tissue, the apparatus comprising
a container comprising a first endwall (bottom), and at least one sidewall,
a detachable second endwall (top) adapted to engage with the container to define a chamber, and
a scaffold adapted to receive a substrate for cells to reside upon,
wherein at least a part of at least one of the first endwall (bottom), the at least one sidewall, or the second endwall (top) comprises a gas permeable material or is adapted to engage with a gas permeable material and is perforated to allow gaseous exchange; and
wherein the apparatus is configurable between (a) a first mode in which the substrate is not disposed in gaseous communication with a gas permeable material, and (b) a second mode in which the substrate is disposed in gaseous communication with a gas permeable material.

For example, in one embodiment the invention relates to an apparatus for culturing cells or tissue, the apparatus comprising
a container comprising a first endwall (bottom), and at least one sidewall,
a detachable second endwall (top) adapted to engage with the container to define a chamber, and
a scaffold adapted to receive a substrate for cells to reside upon,
wherein at least a part of two or more of the first endwall (bottom), the at least one sidewall, and the second endwall (top) comprises a gas permeable material or is adapted to engage with a gas permeable material and is perforated to allow gaseous exchange; and
wherein in a first mode the substrate is not in contact with a gas permeable material, and in a second mode the substrate is in contact with a gas permeable material.

In one embodiment, the scaffold is moveable from a first position to a second position, wherein the second position disposes the substrate at a gas permeable material. In one example, when present at the first position in use, the substrate is submerged.

In one embodiment, in the first mode the scaffold and/or substrate is separated from a gas permeable material by a removable, gas impermeable surface. In one embodiment, the removable gas impermeable surface is removed by dissolution. In one embodiment, the removable gas impermeable surface is physically removed.

In another aspect, the invention relates to an apparatus for culturing cells or tissue, the apparatus comprising
a container comprising a first endwall (bottom) and at least one sidewall, wherein at least a part of the bottom comprises a gas permeable material or is adapted to engage with a gas permeable material and is perforated to allow gaseous exchange;
a detachable second endwall (top) adapted to engage with the container to define a chamber,
wherein at least a part of the second endwall (top) or at least a part of the at least one sidewall comprises a gas permeable material or is adapted to engage with a gas permeable material and is perforated to allow gaseous exchange; and
a scaffold adapted to receive a substrate for cells to reside upon, wherein the scaffold engages with the at least one sidewall to (a) allow substantially linear movement of the scaffold at least partway between the first endwall (bottom) of the chamber and the second endwall (top), and restrict rotation or inversion of the scaffold about an axis perpendicular to the at least one sidewall, or (b) allow rotational movement of the scaffold about an axis perpendicular to the at least one sidewall.

In one embodiment, inversion of the apparatus allows substantially linear movement of the scaffold at least partway between the first endwall (bottom) of the chamber and the second endwall (top) to dispose the substrate at the gas permeable material present in the second endwall (top).

In one embodiment, rotation of the apparatus allows substantially rotational movement of the scaffold about an axis perpendicular to the at least one sidewall to dispose the substrate at the gas permeable material present in the at least one sidewall.

In one embodiment, the invention relates to an apparatus for culturing cells or tissue, the apparatus comprising
   a container comprising a bottom and at least one sidewall, wherein at least a part of the bottom comprises a gas permeable material or is adapted to engage with a gas permeable material and is perforated to allow gaseous exchange;
   a detachable top adapted to engage with the container to define a chamber, wherein at least a part of the top comprises a gas permeable material or is adapted to engage with a gas permeable material and is perforated to allow gaseous exchange; and
   a scaffold adapted to receive a substrate for cells to reside upon, wherein the scaffold engages with the at least one sidewall to (a) allow substantially linear movement of the scaffold at least partway between the bottom of the chamber and the top, and (b) restrict rotation or inversion of the scaffold about an axis perpendicular to the at least one sidewall.

In one embodiment, when in use and a gas permeable material is present in both the bottom and the top, the chamber is liquidly sealable from but in gaseous communication with the environment.

In another aspect, the invention relates to a scaffold for culturing cells or tissue in a culture apparatus comprising at least one gas permeable interface, the scaffold comprising
   a frame defining an interior perimeter and an exterior perimeter, said frame comprising a substantially planar upper surface,
   a substrate for cells to reside upon held in a substantially planar arrangement across the interior perimeter of the frame,
   wherein the scaffold is configured to bring substantially all of the substrate or the cells or tissues present on the substrate into contact with a gas permeable interface when the scaffold is placed in a culture apparatus comprising at least one gas permeable interface.

In one embodiment, the substrate is held in a substantially planar arrangement on the planar upper surface of the frame.

In one aspect, the invention relates to a scaffold for culturing cells or tissue, wherein the scaffold is adapted to receive a substrate for cells to reside upon, the scaffold comprising
   a first frame defining an interior perimeter and an exterior perimeter, said first frame comprising a substantially planar upper surface,
   a second frame defining an interior perimeter and an exterior perimeter, said second frame comprising a substantially planar upper surface,
   wherein the first frame and the second frame detachably engage around at least a part of their perimeters to define an interface to receive and hold the substrate,
   wherein when held the substrate is held in a substantially planar arrangement across the interior perimeter of the first frame,
   and wherein when engaged, the upper surface of the first frame and the upper surface of the second frame are substantially co-planar.

In one embodiment, the dimensions of the interior perimeter of the second frame at its upper surface are greater than the dimensions of the exterior perimeter of the first frame at its upper surface, such that the second frame engages around the exterior perimeter of the first frame at at least the upper surface of the first frame.

In one embodiment, the substrate is held in a substantially planar arrangement across the interior perimeter of the scaffold at the upper surface of the first frame, thereby to allow direct contact of the upper surface of the substrate with, for example, a gas permeable interface.

In various embodiments, the substrate is held between the first frame and the second frame by friction fit engagement of the first frame to the second frame. For example, the friction fit engagement is such that it rigidly clamps the substrate maintain the substrate in a substantially planar arrangement across the interior perimeter of the scaffold. For example, the frames engage to prevent shrinking, stretching or deformation of the substrate, for example when the substrate is contacted with culture media.

In various embodiments, the substrate is held between the first frame and the second frame at least in part by one or more protrusions extending between the first frame and the second frame. In one example, one or more of said one or more protrusions pierce the substrate at a point within the interface formed between the first frame and the second frame on engagement.

In various embodiments, the lower surface of the scaffold comprises at least one section spanning the exterior perimeter of the scaffold and the adjacent interior perimeter, said section having a lower surface which is raised towards the upper surface of the scaffold, wherein said section defines a void when the scaffold is placed on a flat surface. In one embodiment, the section defines a recess 554 provided to allow for easy removal of air bubbles when the scaffold is in submerged culture.

In one embodiment the scaffold comprises a substrate for cells to reside upon.

In one embodiment, the dimensions of the interior perimeter of the scaffold at its upper surface are greater than the dimensions of one or more of the gas permeable interfaces into contact with which the substrate or the cells or tissues present on the substrate held by the scaffold is/are to be brought, such that substantially all of the substrate or the cells or tissues present on the substrate is/are capable of contacting the gas permeable interface.

In various embodiments, the scaffold comprises one or more transverse members spanning the interior perimeter to provide support for the substrate. In one example, the scaffold comprises two or more transverse members. In one example, the scaffold comprises a lattice of transverse members spanning the interior perimeter to provide support for the substrate, for example as depicted in FIG. 11.

In one embodiment, the gas permeable material is a gas permeable membrane.

In one embodiment, the gas permeable material is polydimethylsiloxane.

In one embodiment the scaffold is substantially planar. In one embodiment the scaffold is oriented substantially parallel with the bottom, or the top, or both the bottom and the top.

In one embodiment, the scaffold engages with the at least one sidewall to allow substantially linear movement of the scaffold between the bottom of the container and the top. For example, the scaffold has one or more lugs that engage with one or more complementary grooves in the at least one sidewall to allow translational movement of the scaffold relative to the at least one sidewall but to restrict rotational movement of the scaffold relative to the at least one sidewall.

In one embodiment the scaffold receives the substrate to present culturing surfaces on opposite planar sides of the substrate.

In one embodiment the substrate is a biocompatible material, such as a biocompatible membrane. In one embodiment the substrate is a biodegradable membrane. In various embodiments, the substrate is a co-polymer.

In one embodiment, the substrate is gas permeable. In an alternative embodiment the substrate is gas-impermeable.

For example, the substrate is or comprises poly(lactic co-glycolic acid) (PLGA). In one example, the substrate is or comprises electrospun PLGA.

In one embodiment, the substrate comprises a surface treated to improve cell adhesion, cell migration, or tissue stratification.

In one embodiment, the substrate comprises one or more molecules to aid cell adhesion and/or migration and/or stratification. For example, the substrate comprises one or more proteins, such as one or more basement membrane proteins, a collagen, a fibronectin, a laminin, or a lectin, one or more carbohydrates, such as one or more saccharides, or any combination of two or more thereof.

In other embodiments, the substrate comprises one or more other agents to aid graft viability, maintenance, or longevity. The one or more other agents can be incorporated into the substrate at manufacture, during culturing, or at any point prior to or during surgical implantation of the cells or tissue present on the substrate. Exemplary agents include one or more antibiotics (such as, for example, colloidal silver or colloidal gold, or one or more chemical antibiotics), one or more immunomodulators (such as one or more anti-inflammatory agents), one or more promoters of healing or vascularisation (such as, for example, VEGF), and the like.

In various embodiments the substrate comprises collagen I, fibronectin, collagen IV, collagen VII, laminin 5, one or more adhesion peptides derived from one of the aforementioned proteins, or a combination of any two or more thereof.

In one embodiment the substrate comprises one or more molecules to selectively bind or attract, or promote or enable adhesion of, a specific cell type to the substrate. For example, in one embodiment the substrate comprises one or more molecules to selectively bind epithelial cells, for example, keratinocytes. In another embodiment the substrate comprises one or more molecules to selectively bind fibroblasts.

In various embodiments the substrate comprises one or more cell adhesion molecules such as one or more immunoglobulin superfamily cell adhesion molecules (IgSF CAMs), one or more integrins, one or more cadherins or one or more selectins. In various embodiments the substrate comprises one or more epithelial cadherins (E-cadherins), one or more placental cadherins (P-cadherins), one or more neural cadherins (N-cadherins), one or more retinal cadherins (R-cadherins), one or more brain cadherins (B-cadherins or T-cadherins), or one or more muscle cadherins (M-cadherins), E-selectin, L-selectin, P-selectin, alpha 1 integrin (ITGA1), alpha 2 integrin (ITGA2), alpha 2b integrin (ITGA2b), alpha 3 integrin (ITGA3), alpha 4 integrin (ITGA4), alpha 5 integrin (ITGA5), alpha 6 integrin (ITGA6), alpha 7 integrin (ITGA7), alpha 8 integrin (ITGA8), alpha 9 integrin (ITGA9), alpha 10 integrin (ITGA10), alpha 11 integrin (ITGA11), alpha D integrin (ITGAD), alpha E integrin (ITGAE), alpha L integrin (ITGAL), alpha M integrin (ITGAM), alpha V integrin (ITGAV), alpha X integrin (ITGAX), beta 1 integrin (ITGB1), beta 2 integrin (ITGB2), beta 3 integrin (ITGB3), beta 4 integrin (ITGB4), beta 5 integrin (ITGB5), beta 6 integrin (ITGB6), beta 7 integrin (ITGB7), beta 8 integrin (ITGB8), or a combination of any two or more thereof.

In one embodiment, the substrate comprises one or more molecules to aid epithelial stratification, for example, epidermal stratification.

In one embodiment at least a part of the scaffold comprises a gas permeable material and/or is adapted to engage with a gas permeable substrate and is perforated to allow gaseous exchange across the gas permeable substrate.

In various embodiments, the container or detachable top comprises at least one fluidly-sealable access port. For example, the at least one sidewall comprises at least one fluidly-sealable access port.

In various embodiments, the apparatus is sterilisable, including, for example, by autoclaving or gamma irradiation.

In one embodiment, when the apparatus is in a first mode (for example, an upright orientation) the scaffold and substrate are disposed within the chamber and the substrate is submerged.

In one embodiment, when the apparatus is in a second mode (for example, an inverted or rotated orientation) the substrate is disposed at a gas permeable material. For example, in a second mode the scaffold and substrate define the bottom of the chamber to comprise a gas permeable interface.

In one embodiment, in use the apparatus is configured so that the chamber holds a volume of culture media sufficient to submerge the substrate when the apparatus is in a first mode (for example, in an upright orientation).

In one embodiment, in use the apparatus is configured in a second mode wherein the substrate is at or adjacent a gas permeable material. For example, in one embodiment the substrate comprises a gas permeable interface when the apparatus is in a second mode (e.g., an inverted or rotated orientation).

In another aspect, the invention relates to a method of culturing cells, the method comprising
  a) providing a suspension comprising cells to be cultured in an amount of tissue culture medium sufficient to support cell growth;
  b) introducing the suspension into a cell culture apparatus, wherein the apparatus comprises a container comprising a first endwall (bottom), at least one sidewall, and a detachable second endwall (top) adapted to engage with the container to define a chamber, and a scaffold adapted to receive a substrate for cells to reside upon, wherein at least a part of at least the first endwall (bottom), the at least one sidewall, or the second endwall (top) comprises a gas permeable material or is adapted to engage with a gas permeable material and is perforated to allow gaseous exchange; and wherein the apparatus is in a first mode in which the substrate is submerged in the suspension, and optionally is disposed in gaseous communication with a gas permeable material,
  c) incubating the cell culture apparatus containing the suspension for a time sufficient for at least some of the cells to adhere to the substrate,
  d) adapting the cell culture apparatus to a second mode in which the substrate is optionally disposed in gaseous communication with a gas permeable material, and e) incubating the cell culture apparatus for a time sufficient to allow one or more of cell confluence, cell proliferation, cell differentiation, tissue stratification, or tissue growth.

In one embodiment in step b) the apparatus is in a first mode in which the substrate is disposed in gaseous communication with a gas permeable material. In one embodiment in step d) the apparatus is in a second mode in which the substrate is disposed in gaseous communication with a gas permeable material.

In another aspect, the invention relates to a method for culturing one or more confluent layers of cells on a substrate, the method comprising the steps of:

a) providing a suspension comprising the cells to be cultured in an amount of tissue culture medium sufficient to support cell growth;

b) introducing the suspension into a cell culture apparatus, wherein the apparatus comprises a container comprising a first endwall (bottom), at least one sidewall, and a detachable second endwall (top) adapted to engage with the container to define a chamber, and a scaffold adapted to receive a substrate for cells to reside upon, wherein at least a part of the first endwall (bottom), the at least one sidewall, or the second endwall (top) comprises a gas permeable material or is adapted to engage with a gas permeable material and is perforated to allow gaseous exchange; and wherein the apparatus is in a first mode in which the substrate is submerged in the suspension and is not in gaseous communication with a gas permeable material, c) incubating the cell culture apparatus containing the suspension for a time sufficient for at least some of the cells to adhere to the substrate, d) adapting the cell culture apparatus to a second mode in which the substrate is disposed in gaseous communication with the gas permeable material, and e) incubating the cell culture apparatus for a time sufficient to form one or more confluent layers of cells, wherein said one or more confluent layers of cells are disposed over at least part of the substrate.

In various embodiments step e) comprises incubating the cell culture apparatus for a time sufficient to allow one or more of cell differentiation or cell proliferation.

In various embodiments, the apparatus is an apparatus of the invention.

In one embodiment, the cell suspension is introduced via an access port present in the chamber, for example, an access port present in the container.

In another embodiment, the cell suspension is introduced to the container prior to attaching the top.

In one embodiment, the cells to be cultured are anchorage-dependent cells.

In one embodiment, the cells comprise epithelial cells. In one embodiment, the cells comprise keratinocytes. In one embodiment, the cells comprise fibroblasts. In one embodiment, the cells comprise keratinocytes and fibroblasts.

In one embodiment the cell suspension comprises a population of cells obtained from a tissue digest.

In one embodiment, the method comprises the following additional steps between steps d) and e)

f) introducing a second suspension comprising cells to be cultured, for example via the access port, and g) incubating the cell culture apparatus containing the second suspension for a time sufficient for at least some of the cells in the second suspension to adhere to the substrate, and optionally h) adapting the cell culture apparatus to dispose the substrate or the cells in gaseous communication with a gas permeable material.

In one embodiment, the method comprises one or more repeats of steps f) to h).

In one embodiment, the second suspension comprises one or more cell types that differ from those present in the first suspension. For example, in one embodiment the first suspension comprises fibroblasts, and the second suspension comprises keratinocytes.

In one embodiment, the substrate is biocompatible. In one embodiment, the substrate is biodegradable.

In another aspect, the invention relates to a method for culturing tissue, for example, epithelial tissue, the method comprising the steps of:

a) providing a suspension comprising epithelial cells in an amount of tissue culture medium sufficient to support cell growth;

b) introducing the suspension into the cell culture apparatus, the apparatus introducing the suspension into a cell culture apparatus, wherein the apparatus comprises a container comprising a first endwall (bottom), at least one sidewall, and a detachable second endwall (top) adapted to engage with the container to define a chamber, and a scaffold adapted to receive a substrate for cells to reside upon, wherein at least a part of the first endwall (bottom), the at least one sidewall, or the second endwall (top) comprises a gas permeable material or is adapted to engage with a gas permeable material and is perforated to allow gaseous exchange; and wherein the apparatus is in a first mode in which the substrate is submerged in the suspension and is optionally in gaseous communication with a gas permeable material, c) incubating the cell culture apparatus containing the suspension for a time sufficient for at least some of the epithelial cells to adhere to the substrate, d) adapting the cell culture apparatus to a second mode in which the substrate is and/or the cells are disposed in gaseous communication with the gas permeable material, and e) incubating the cell culture apparatus for a time sufficient to allow cell differentiation, proliferation or stratification or epithelial tissue development to occur.

In one embodiment the method comprises one or more of the following steps following step b):

f) removing the tissue culture medium from the apparatus, g) washing the surface of the substrate to remove unadhered cells, and/or h) adding fresh tissue culture medium to the apparatus.

In one embodiment, the epithelial cells are keratinocytes.

In one embodiment the suspension further comprises a second population of cells, for example, fibroblasts.

In one embodiment in step b) the apparatus is in a first mode in which the substrate optionally is disposed in gaseous communication with a gas permeable material; and in step d) the apparatus is in a second mode in which the epithelial cells are disposed in gaseous communication with a gas permeable material. For example, the epithelial cells are in direct contact with a gas permeable material.

In another aspect, the invention relates to a method for culturing stratified epidermal tissue or full thickness skin tissue, the method comprising the steps of:

a) providing a suspension comprising keratinocytes and fibroblasts in an amount of tissue culture medium sufficient to support cell growth;

b) introducing the suspension into the cell culture apparatus, the apparatus introducing the suspension into a cell culture apparatus, wherein the apparatus comprises a container comprising a first endwall (bottom), at least one sidewall, and a detachable second endwall (top) adapted to engage with the container to define a chamber, and a scaffold adapted to receive a substrate for cells to reside upon,
wherein at least a part of the first endwall (bottom), the at least one sidewall, or the second endwall (top) comprises a gas permeable material or is adapted to engage with a gas permeable material and is perforated to allow gaseous exchange; and
wherein the apparatus is in a first mode in which the substrate is submerged in the suspension and is not in gaseous communication with a gas permeable material,
c) incubating the cell culture apparatus containing the suspension for a time sufficient for at least some of the keratinocytes and/or fibroblasts to adhere to the substrate,
d) adapting the cell culture apparatus to a second mode in which the substrate is and/or the cells are disposed in gaseous communication with the gas permeable material, and
e) incubating the cell culture apparatus for a time sufficient to allow epidermal stratification to occur.

In another aspect, the invention relates to a method for culturing stratified epithelial tissue, the method comprising the steps of:
a) providing a first suspension comprising cells in an amount of tissue culture medium sufficient to support cell growth;
b) introducing the first suspension into a cell culture apparatus, wherein the apparatus comprises a container comprising a first endwall (bottom), at least one sidewall, and a detachable second endwall (top) adapted to engage with the container to define a chamber, wherein the chamber comprises an injection port, and a scaffold adapted to receive a substrate for cells to reside upon,
wherein at least a part of the first endwall (bottom), the at least one sidewall, or the second endwall (top) comprises a gas permeable material or is adapted to engage with a gas permeable material and is perforated to allow gaseous exchange; and
wherein the apparatus is in a first mode in which the substrate is submerged in the suspension and optionally is in gaseous communication with a gas permeable material,
c) incubating the cell culture apparatus containing the suspension for a time sufficient for at least some of the cells in the first suspension to adhere to the substrate;
d) optionally adapting the cell culture apparatus to a second mode in which the substrate is not disposed in gaseous communication with the gas permeable material,
e) introducing a second suspension comprising epithelial cells into the cell culture apparatus through the injection port,
f) incubating the cell culture apparatus containing the second suspension for a time sufficient for at least some of the epithelial cells to adhere to the substrate,
g) adapting the cell culture apparatus to the first mode in which the substrate and/or the epithelial cells are disposed in gaseous communication with the gas permeable material, and
h) incubating the cell culture apparatus for a time sufficient for epithelial stratification to occur.

In another aspect, the invention relates to a method for culturing full thickness skin tissue or stratified epidermal tissue, the method comprising the steps of:
a) providing a suspension comprising fibroblasts in an amount of tissue culture medium sufficient to support cell growth;
b) introducing the suspension into a cell culture apparatus, wherein the apparatus comprises a container comprising a first endwall (bottom), at least one sidewall, and a detachable second endwall (top) adapted to engage with the container to define a chamber, wherein the chamber comprises an injection port, and a scaffold adapted to receive a substrate for cells to reside upon,
wherein at least a part of the first endwall (bottom), the at least one sidewall, or the second endwall (top) comprises a gas permeable material or is adapted to engage with a gas permeable material and is perforated to allow gaseous exchange; and
wherein the apparatus is in a first mode in which the substrate is submerged in the suspension and optionally is in gaseous communication with a gas permeable material,
c) incubating the cell culture apparatus containing the suspension for a time sufficient for at least some of the fibroblasts to adhere to the substrate;
d) optionally adapting the cell culture apparatus to a second mode in which the substrate is not disposed in gaseous communication with the gas permeable material,
e) introducing a suspension comprising keratinocytes in an amount of tissue culture medium sufficient to support cell growth into the cell culture apparatus through the injection port,
f) incubating the cell culture apparatus containing the suspension for a time sufficient for at least some of the keratinocytes to adhere to the substrate,
g) adapting the cell culture apparatus to the first mode in which the substrate and/or the keratinocytes are disposed in gaseous communication with the gas permeable material, and
h) incubating the cell culture apparatus for a time sufficient for epidermal stratification to occur.

In one embodiment, the adaption to a second mode in step (d) exposes the surface of the substrate opposite that to which the fibroblasts are anchored to the gas permeable material.

In one embodiment the method comprises
a) providing a suspension comprising fibroblasts in an amount of tissue culture medium sufficient to support cell growth;
b) introducing the suspension into a cell culture apparatus, wherein the apparatus comprises a container comprising a first endwall (bottom), at least one sidewall, and a detachable second endwall (top) adapted to engage with the container to define a chamber, wherein the chamber comprises an injection port, and a scaffold adapted to receive a substrate for cells to reside upon,
c) wherein at least a part of the first endwall (bottom), the at least one sidewall, or the second endwall (top) comprises a gas permeable material or is adapted to engage with a gas permeable material and is perforated to allow gaseous exchange; and
wherein the apparatus is in a first mode in which the substrate is submerged in the suspension, d) incubating the cell culture apparatus containing the suspension for a time sufficient for at least some of the fibroblasts to adhere to the substrate and optionally to allow the fibroblasts to proliferate to form one or more dermal layers;
e) introducing a suspension comprising keratinocytes in an amount of tissue culture medium sufficient to support cell growth into the cell culture apparatus through the injection port,
f) incubating the cell culture apparatus containing the suspension for a time sufficient for at least some of the keratinocytes to adhere to the substrate,
g) adapting the cell culture apparatus to a second mode in which the keratinocytes are disposed in gaseous communication with the gas permeable material, and
h) incubating the cell culture apparatus for a time sufficient for epidermal stratification to occur.

In another embodiment the method comprises:
a) providing a suspension comprising fibroblasts in an amount of tissue culture medium sufficient to support cell growth;
b) introducing the suspension into a cell culture apparatus, wherein the apparatus comprises a container comprising a first endwall (bottom), at least one sidewall, and a detachable second endwall (top) adapted to engage with the container to define a chamber, wherein the chamber comprises an injection port, and a scaffold adapted to receive a substrate for cells to reside upon,
wherein at least a part of the first endwall (bottom), the at least one sidewall, or the second endwall (top) comprises a gas permeable material or is adapted to engage with a gas permeable material and is perforated to allow gaseous exchange; and
wherein the apparatus is in a first mode in which the substrate is submerged in the suspension,
c) incubating the cell culture apparatus containing the suspension for a time sufficient for at least some of the fibroblasts to adhere to the substrate and optionally to allow the fibroblasts to proliferate to form one or more dermal layers;
d) adapting the cell culture apparatus to a second mode in which the fibroblasts are disposed in gaseous communication with the gas permeable material,
e) introducing a suspension comprising keratinocytes in an amount of tissue culture medium sufficient to support cell growth into the cell culture apparatus through the injection port,
f) incubating the cell culture apparatus containing the suspension for a time sufficient for at least some of the keratinocytes to adhere to the substrate,
g) adapting the cell culture apparatus to the first mode in which the keratinocytes are disposed in gaseous communication with the gas permeable material, and
h) incubating the cell culture apparatus for a time sufficient for epidermal stratification to occur.

In one embodiment, the substrate is impermeable to the one or more cells.

In another embodiment, the substrate is permeable to one or more cells.

In one embodiment, the cell culture apparatus is incubated for a time sufficient to allow the migration of at least some fibroblasts into or through the substrate.

In one embodiment the cell culture apparatus is incubated for a time sufficient to allow for proliferation of at least some of the fibroblasts.

In one embodiment the cell culture apparatus is incubated for a time sufficient for the fibroblasts to produce a thickened dermis. In another embodiment the cell culture apparatus is incubated for a time sufficient for extracellular matrix deposition to occur.

In various embodiments the cell culture apparatus is incubated for a period of at least one week, for example, at least two weeks, or at least three weeks. In certain embodiments, the cell culture apparatus is incubated for a period of at least about one month, for example, at least about two months.

In another aspect, the invention relates to a method for culturing stratified epithelial tissue, the method comprising the steps of:
a) providing a suspension comprising epithelial cells in an amount of tissue culture medium sufficient to support cell growth;
b) introducing the suspension into a cell culture apparatus, wherein the apparatus comprises a container comprising a first endwall (bottom), at least one sidewall, and a detachable second endwall (top) adapted to engage with the container to define a chamber, wherein the chamber comprises a scaffold adapted to receive a substrate for cells to reside upon,
wherein at least a part of the first endwall (bottom), the at least one sidewall, or the second endwall (top) comprises a gas permeable material or is adapted to engage with a gas permeable material and is perforated to allow gaseous exchange; and
wherein the apparatus is in a first mode in which the substrate is submerged in the suspension and is not in gaseous communication with a gas permeable material,
c) incubating the cell culture apparatus containing the suspension for a time sufficient for at least some of the epithelial cells to adhere to the substrate;
d) adapting the cell culture apparatus to a second mode in which the substrate is disposed in gaseous communication with at the gas permeable material,
e) incubating the cell culture apparatus for a time sufficient for epithelial stratification to occur.

In another aspect, the invention relates to a method for culturing stratified epidermal tissue, the method comprising the steps of:
a) providing a suspension comprising keratinocytes in an amount of tissue culture medium sufficient to support cell growth;
b) introducing the suspension into a cell culture apparatus, wherein the apparatus comprises a container comprising a first endwall (bottom), at least one sidewall, and a detachable second endwall (top) adapted to engage with the container to define a chamber, wherein the chamber comprises a scaffold adapted to receive a substrate for cells to reside upon,
wherein at least a part of the first endwall (bottom), the at least one sidewall, or the second endwall (top) comprises a gas permeable material or is adapted to engage with a gas permeable material and is perforated to allow gaseous exchange; and
wherein the apparatus is in a first mode in which the substrate is submerged in the suspension and is not in gaseous communication with a gas permeable material,
c) incubating the cell culture apparatus containing the suspension for a time sufficient for at least some of the keratinoctyes to adhere to the substrate;
d) adapting the cell culture apparatus to a second mode in which the substrate is disposed in gaseous communication with at the gas permeable material, e) incubating the cell culture apparatus for a time sufficient for epidermal stratification to occur.

In one embodiment, the substrate is impermeable to the one or more cells.

In another embodiment, the substrate is permeable to one or more cells.

In one embodiment one or more layers of fibroblasts are disposed over at least a part of the surface of the substrate.

In a further aspect, the invention relates to a method for culturing stratified epithelial tissue, the method comprising the steps of:
- a) providing adhered epithelial cells or tissue comprising epithelial cells disposed over at least a part of the surface of a substrate,
- b) introducing the adhered epithelial cells or tissue comprising epithelial cells into a cell culture apparatus, wherein the apparatus comprises a container comprising a first endwall (bottom), at least one sidewall, and a detachable second endwall (top) adapted to engage with the container to define a chamber, and wherein the cell culture apparatus contains culture media;
  - wherein at least a part of the first endwall (bottom), the at least one sidewall, or the second endwall (top) comprises a gas permeable material or is adapted to engage with a gas permeable material and is perforated to allow gaseous exchange; and
  - wherein the apparatus is in a first mode in which the substrate, adhered epithelial cells and/or tissue comprising epithelial cells is submerged in the media and is in gaseous communication with a gas permeable material,
- c) incubating the cell culture apparatus containing the adhered epithelial cells or tissue comprising epithelial cells for a time sufficient for epithelial stratification to occur.

In one embodiment the adhered epithelial cells are keratinocytes and the stratified epithelial tissue is stratified epidermal tissue.

In a further aspect, the invention relates to a method for culturing full thickness skin tissue, the method comprising the steps of:
- a) providing adhered cells or tissue disposed over at least a part of the surface of a substrate,
- b) introducing the adhered cells or tissue into a cell culture apparatus, wherein the apparatus comprises a container comprising a first endwall (bottom), at least one sidewall, and a detachable second endwall (top) adapted to engage with the container to define a chamber, and wherein the cell culture apparatus contains culture media;
  - wherein at least a part of the first endwall (bottom), the at least one sidewall, or the second endwall (top) comprises a gas permeable material or is adapted to engage with a gas permeable material and is perforated to allow gaseous exchange; and
  - wherein the apparatus is in a first mode in which the substrate, adhered cells and/or tissue is submerged in the media and is in gaseous communication with a gas permeable material,
- c) incubating the cell culture apparatus containing the adhered cells or tissue for a time sufficient for epidermal stratification and/or generation of full thickness skin to occur.

In one embodiment the adhered cells or tissue comprises one or more populations of cells.

In one embodiment, the adhered cells, for example, keratinocytes, are adhered to at least a part of the surface of a substrate.

In one embodiment the adhered cells or tissue comprises fibroblasts. In another embodiment the adhered cells or tissue comprises keratinocytes. In a further embodiment the adhered cells or tissue comprises fibroblasts and keratinocytes.

In one embodiment the keratinocytes are undifferentiated.

In one embodiment the substrate engages with a scaffold disposable within the chamber. For example, the chamber comprises a scaffold adapted to receive the substrate. In another example, the scaffold receives the substrate prior to introduction of the scaffold to the chamber.

In another aspect, the invention relates to a method for culturing cells on a biocompatible substrate, the method comprising the steps of:
- a) providing a chamber having at least one gas permeable surface, wherein the chamber comprises a scaffold adapted to receive a substantially planar biocompatible gas permeable substrate, the scaffold capable of substantially linear movement from a first position to a second position at or adjacent and in gaseous communication with the gas permeable surface,
- b) providing the chamber in a first mode so the scaffold is in the first position defining a liquid impermeable volume within the chamber and introducing to the volume a suspension comprising cells to be cultured,
- c) introducing a first suspension comprising cells in an amount of tissue culture medium sufficient to support cell growth into the cell culture apparatus,
- d) incubating the chamber for a time sufficient to allow at least some of the cells to adhere to the substrate,
- e) providing the chamber in a second mode so the scaffold is in the second position defining a liquid impermeable volume within the chamber and wherein the substrate is in gaseous communication with the gas permeable surface, and
- f) optionally introducing a second suspension comprising cells in an amount of tissue culture medium sufficient to support cell growth into the cell culture apparatus,
- g) incubating the chamber for a time sufficient to allow the formation of one or more confluent layers of cells, wherein said one or more confluent layers of cells are disposed over at least part of the substrate.

In one embodiment, the method is a method of culturing epithelial cells, epidermal cells, or both epithelial and epidermal cells.

In one embodiment, the first suspension comprises fibroblasts and keratinocytes.

In another aspect, the invention relates to a method for culturing cells on a biocompatible substrate, the method comprising the steps of:
- a) providing a chamber having at least two gas permeable surfaces, wherein the chamber comprises a scaffold adapted to receive a substantially planar biocompatible gas permeable substrate, the scaffold capable of substantially linear movement from a first position at or adjacent and in gaseous communication with the first gas permeable surface to a second position at or adjacent and in gaseous communication with the second gas permeable surface,
- b) providing the chamber in a first mode so the scaffold is in the first position defining a liquid impermeable volume within the chamber and wherein the substrate is in gaseous communication with the first gas permeable surface, c) introducing a first suspension comprising cells in an amount of tissue culture medium sufficient to support cell growth into the cell culture apparatus,
d) incubating the chamber for a time sufficient to allow at least some of the cells to adhere to the substrate,
e) providing the chamber in a second mode so the scaffold is in the second position defining a liquid impermeable volume within the chamber and wherein the substrate is in gaseous communication with the second gas permeable surface, and
f) introducing a second suspension comprising cells in an amount of tissue culture medium sufficient to support cell growth into the cell culture apparatus,
g) incubating the chamber for a time sufficient to allow at least some of the cells to adhere to the substrate and to allow the formation of one or more confluent layers of cells, wherein said one or more confluent layers of cells are disposed over at least part of the substrate.

In one embodiment, the method is a method of culturing epithelial cells, epidermal cells, or both epithelial and epidermal cells.

In one embodiment, the first cell suspension comprises fibroblasts. In one embodiment, the second cell suspension comprises keratinocytes.

In one embodiment, the formation of one or more confluent layers of cells is the formation of one or more stratified epidermal tissues.

In one embodiment, the formation of one or more confluent layers of cells is the formation of full thickness skin.

In one embodiment, the movement of the scaffold is substantially linear movement from the first position at or adjacent and in gaseous communication with the first gas permeable surface to the second position at or adjacent and in gaseous communication with the second gas permeable surface. In one embodiment, said linear movement is without significant rotation or inversion of the scaffold about an axis perpendicular to the linear movement.

In another aspect, the invention relates to a method of producing stratified epidermal tissue the method comprising
a) providing a substrate wherein adhered keratinocytes are disposed over at least a part of a surface of the substrate;
b) providing a cell culture apparatus comprising at least one gas permeable interface;
c) introducing the substrate into the apparatus such that the keratinocytes are in contact with the gas permeable interface,
d) incubating the cell culture apparatus for a time sufficient to allow epidermal stratification to occur.

In one embodiment the method comprises providing a substrate wherein adhered fibroblasts are disposed over at least a part of a surface of the substrate. In one embodiment adhered keratinocytes and adhered fibroblasts are disposed over at least a part of one surface of the substrate. In one embodiment adhered keratinocytes are disposed over at least a part of one surface of the substrate and adhered fibroblasts are disposed over at least a part of an opposing surface.

In one embodiment the method is a method of producing tissue comprising stratified epidermis and dermis. In one embodiment the method is a method of producing full thickness skin.

In one embodiment, the biocompatible substrate is a membrane and the scaffold is adapted to hold the membrane under tension.

In various embodiments, the substrate is or comprises one or more of the following: acellular de-epithelialised dermis (alloderm); dermis; collagen including collagen gel and tissues comprising collagen; tissue or cells of an epidermal or epithelial lineage, including tissues or cells from umbilical cord, placenta, mucosa, the digestive tract; fibronectin/fibrin; platelet rich plasma; Matrigel; components of and tissues comprising extracellular matrix including extracellular matrix secreted by cells such as fibroblasts; hyaluronic acid; electrospun biocompatible materials including PLGA; biocompatible polymers or combinations of biocompatible polymers, particularly those capable of being electrospun, including polyacrylic acid, poly L Lysine, collagen, gelatin, nylon, and polyesters; gelatine; peptide hydrogels; polyglactin scaffolds; dermagraft; elastin; chitosan; fibroin; spider silk; agarose, and any combinations of two or more thereof.

It will be appreciated that the cells and tissues recited above may be from any animal source, including human, equine, porcine, ovine, murine, canine, feline and bovine.

Those of skill in the art will, on reading the present disclosure, recognise that a substrate comprising one or more biologically derived products will generally provide appropriate stimulation for epidermal stratification to occur in certain embodiments of the invention without further modification, while substrates comprising one or more synthetic materials will typically require modification, such as a coating, to provide stimulus for epidermal stratification.

It will further be appreciated that the methods of the invention are amenable to the culturing of any animal cells. Particularly contemplated are mammalian cells, including human.

The methods of the invention can be used to prepare tissues including epithelium, for example a single cell-thick layer of keratinocytes, stratified epithelium comprising at least two of the stratum basale, stratum spinosum, stratum granulosum, stratum lucidum and stratum corneum, and full thickness skin comprising dermal and epidermal layers.

In various embodiments, the gas permeable material is selected for optimal gaseous exchange and/or cellular growth, proliferation, and/or stratification.

In one embodiment, the gas permeable material is a gas permeable membrane having a thickness of less than 250 µm.

In various embodiments, particularly those in which a single cellular suspension is introduced into the cell culture apparatus, the apparatus is of a volume sufficient to contain growth medium sufficient for at least 10 days, for example at least 14 days, at least 15 days, at least 16 days or at least 17 days or longer.

In one aspect, the invention provides cells, for example, epithelial cells, keratinocytes, fibroblasts or keratinocytes and fibroblasts, prepared by a method or in a culture apparatus as herein described.

In one embodiment the keratinocytes are differentiated keratinocytes.

In one embodiment the cells are adhered to a substrate.

In a further aspect, the invention provides tissue, for example, epithelial tissue, stratified epithelial tissue, epidermis, stratified epidermis, stratified epidermis and dermis, or full thickness skin, prepared by a method or in a culture apparatus as herein described.

In another aspect the invention provides tissue comprising a dermal layer comprising fibroblasts, a stratified epidermal layer comprising keratinocytes and a biocompatible substrate, prepared by a method or in a culture apparatus as herein described.

In one embodiment, the biocompatible substrate is a biodegradable substrate. In one example, the biodegradeable substrate is present between the dermal and epidermal layers.

In one embodiment the tissue comprises a dermal layer comprising fibroblasts that are at least partially embedded in, or attached to, the substrate, and an epidermal layer. In another embodiment the tissue comprises a substrate, a dermal layer attached to one surface of the substrate and an epidermal layer attached to the opposing surface of the substrate. In another embodiment the tissue comprises an epidermal layer, a substrate attached on one surface of the epidermal layer and a dermal layer attached to the opposing surface of the epidermal layer.

In various embodiments the dermal layer, the epidermal layer or the dermal layer and the epidermal layer are embedded in, or attached to, the substrate.

In another aspect, the invention relates to the use of tissue, for example epidermis, stratified epidermis, stratified epidermis and dermis, or full thickness skin, prepared in a method as herein described in the treatment of tissue damage in a subject in need thereof.

In various embodiments the treatment is of a wound, a burn, a scar including a surgical scar.

In a further aspect, the invention provides a method of treating tissue damage in a patient in need thereof, the method comprising the steps of
a) providing an apparatus of the present invention in which tissue, such as epithelial tissue, stratified epithelial tissue, epidermis, stratified epidermis, stratified epidermis and dermis, or full thickness skin, has been grown, for example in a method as herein described,
b) recovering under sterile conditions the tissue from the apparatus, and
c) applying the tissue to the subject.

Generally, the application of tissue to the subject will be by surgery. In one embodiment, recovery under sterile conditions is during or immediately prior to surgery, for example in the surgical suite.

Generally, the application of tissue to the subject will be at or adjacent the site of tissue damage.

In various embodiments, the tissue damage is selected from a wound, a burn, a scar, a surgical site, and the like.

In various embodiments the epithelial tissue is applied to a region of the digestive tract, integumentary system, reproductive tract, respiratory tract, sensory system, or urinary tract. In various embodiments the epithelial tissue is applied to, or forms, the submandibular gland, attached gingiva, dorsum of tongue, hard palate, oesophagus, stomach, large intestine, small intestine, rectum, anus, gallbladder, thyroid follicle, skin, sweat gland duct, mesothelium of body cavities, ovary, fallopian tube, uterus, cervix, vagina, labia majora, tubuli recti, rete testis, ductuli efferentes, epididymis, vas deferens, ejaculatory duct, bulbourethral gland, seminal vesicle, oropharynx, larynx, larynx, vocal cord, trachea, respiratory bronchiole, cornea, nose, proximal convoluted tubule of the kidney, ascending thin limb of the kidney, distal convoluted tubule of the kidney, collecting duct of the kidney, renal pelvis, ureter, urinary bladder, prostatic urethra, membranous urethra, penile urethra, or external urethral orifice.

In a further aspect, the invention provides a method of engineering a structure comprising epithelial tissue the method comprising the steps of
a) providing an apparatus of the present invention in which tissue, such as epithelial tissue, stratified epithelial tissue, epidermis, or stratified epidermis, has been grown, for example in a method as herein described,
b) recovering under sterile conditions the tissue from the apparatus, and
c) manipulating the recovered tissue to form the structure.

In a further aspect the invention provides a method of engineering a structure comprising epithelial tissue the method comprising the steps of
a) providing an apparatus of the present invention in which tissue, such as epithelial tissue, stratified epithelial tissue, epidermis, or stratified epidermis, has been grown, for example in a method as herein described,
b) recovering under sterile conditions the tissue from the apparatus,
c) applying the tissue to the subject, and
d) manipulating the tissue to form the structure.

In various embodiments the structure comprises a structure of the digestive tract, integumentary system, reproductive tract, respiratory tract, sensory system, or urinary tract. In various embodiments the structure comprises a duct of the submandibular gland, attached gingiva, dorsum of tongue, hard palate, oesophagus, stomach, large intestine, small intestine, rectum, anus, gallbladder, thyroid follicle, skin, sweat gland duct, mesothelium of body cavities, ovary, fallopian tube, uterus, cervix, vagina, labia majora, tubuli recti, rete testis, ductuli efferentes, epididymis, vas deferens, ejaculatory duct, bulbourethral gland, seminal vesicle, oropharynx, larynx, larynx, vocal cord, trachea, respiratory bronchiole, cornea, nose, proximal convoluted tubule of the kidney, ascending thin limb of the kidney, distal convoluted tubule of the kidney, collecting duct of the kidney, renal pelvis, ureter, urinary bladder, prostatic urethra, membranous urethra, penile urethra, or external urethral orifice.

In a further aspect, the invention provides a method of testing the toxicity of a compound or composition to a tissue, the method comprising the steps of
a) providing an apparatus of the present invention in which tissue, such as epithelial tissue, stratified epithelial tissue, epidermis, stratified epidermis, stratified epidermis and dermis, or full thickness skin, has been grown, for example in a method as herein described,
b) applying the compound or composition to the tissue, and
c) assessing whether tissue damage or cell death to the tissue occurs.

In a further aspect, the invention provides a method of testing the tissue permeability, for example, the transdermal permeability, of a compound or composition, the method comprising the steps of
a) providing an apparatus of the present invention in which tissue, such as epidermis, stratified epidermis, stratified epidermis and dermis, or full thickness skin, has been grown, for example in a method as herein described,
b) applying the compound or composition to the tissue, and
c) assessing the permeability of the compound or composition through the tissue.

In a further aspect, the invention provides a method of testing the efficacy of a compound or a cosmetic, therapeutic or nutraceutical composition for effecting a change in tissue, the method comprising the steps of
a) providing an apparatus of the present invention in which tissue, such as epidermis, stratified epidermis, stratified epidermis and dermis, or full thickness skin, has been grown, for example in a method as herein described,
b) applying the compound or composition to the tissue, and
c) assessing the efficacy of the compound or composition for effecting a change in the tissue.

In one embodiment the method further comprises the step of recovering the tissue from the apparatus following step a). In an alternative embodiment the method comprises applying the compound or composition to tissue in situ within the apparatus.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

BRIEF DESCRIPTION OF THE DRAWINGS

The invention will now be described by way of example only and with reference to the drawings in which:

FIG. 13 shows a top perspective view of an alternative embodiment of the lower member of the scaffold of FIG. 9;

FIG. 14 shows A) a cross section of the lower scaffold member of the embodiment shown in FIG. 13 taken through plane B-B; and (B) the same view showing the scaffold engaging a substrate anchored by an upper scaffold member;

DETAILED DESCRIPTION OF THE INVENTION

Figure 1:
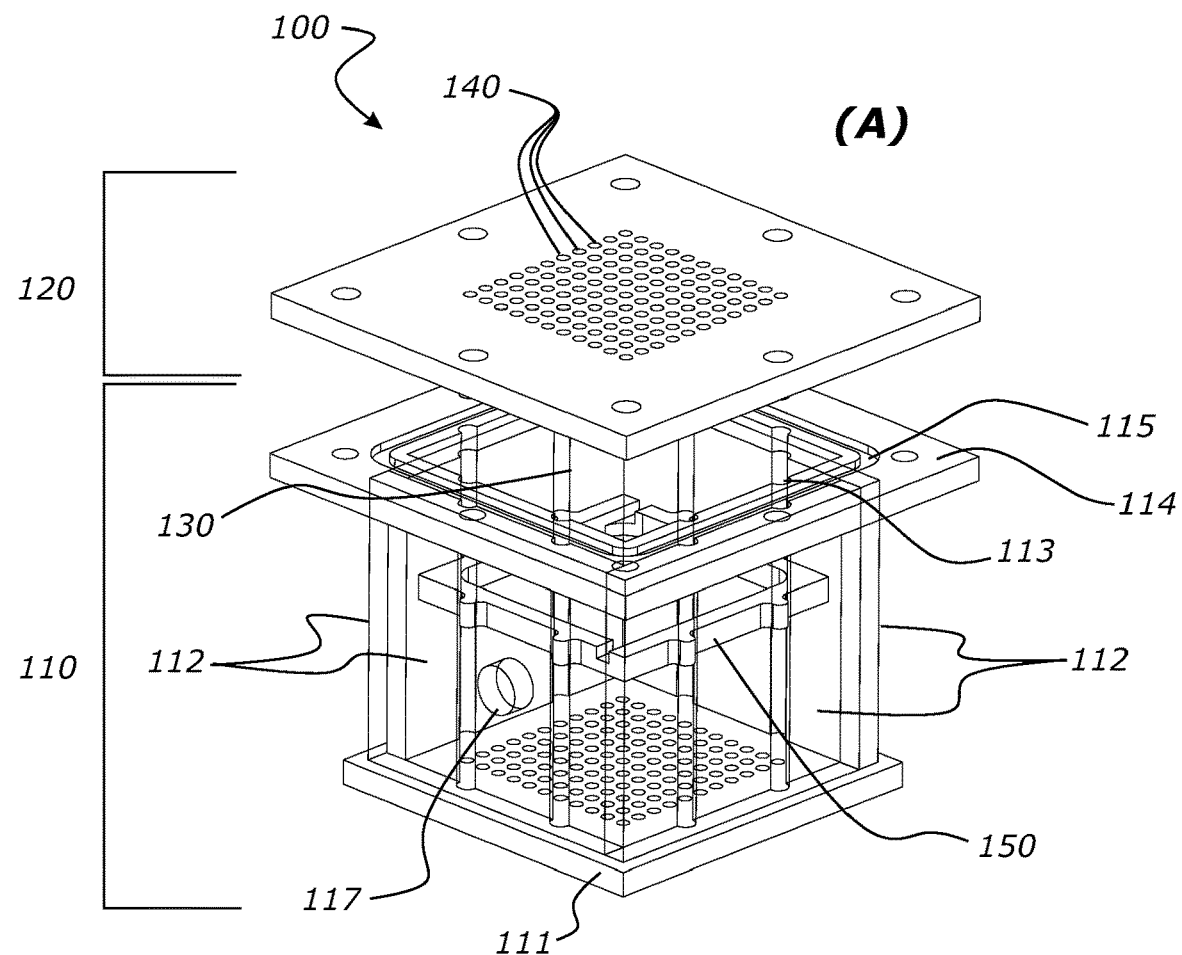
FIG. 1 is two exploded perspective views of a first embodiment of the apparatus.
Figure 1:
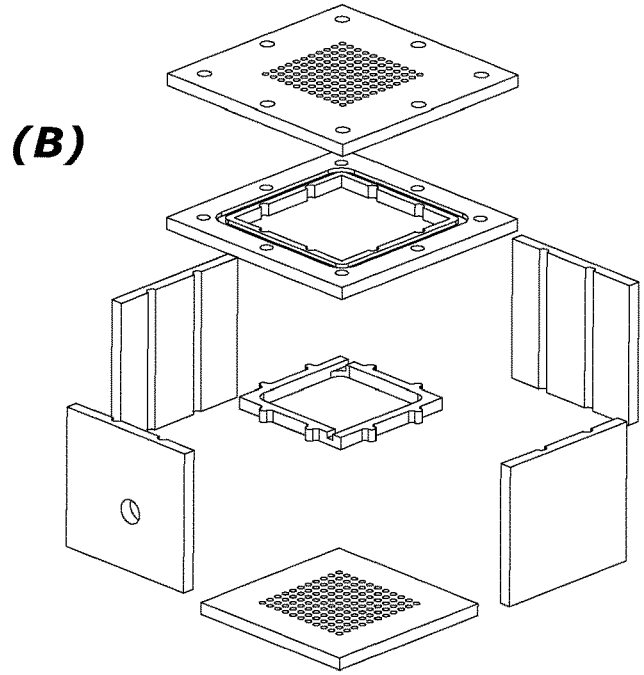

The present invention relates to an apparatus and method for culturing cells. The apparatus comprises a container comprising a first endwall and at least one sidewall, and a detachable second endwall wherein at least a part of two or more walls comprises a gas permeable material or is adapted to engage with a gas permeable material and is perforated to allow gaseous exchange.

The present invention further relates to tissue prepared by a method or in a culture apparatus described herein, or to the use of such tissue for the treatment of tissue damage in a patient in need thereof.

The apparatus and methods described herein provides for the culture of cells and tissues, for example, epithelial cells, stratified epithelial cells, keratinocytes, fibroblasts and/or epithelial tissue such as skin, under conditions that mimic an air-liquid interface. The conditions provide a high oxygen environment that promotes epithelial cell differentiation and/or stratification, and/or the growth of multicellular layers or multilayer tissues. The apparatus and methods of the invention dispose growing cells and tissues in gaseous communication with, for example, at, a gas permeable interface.

Embodiments of the methods and apparatus of the invention have numerous advantages, including but not limited to
- practical and efficient engineering of cells and tissues,
- production of fully synthetic tissues without the use of xenobiotic substances such as animal-derived compounds or substances,
- reduced cost of manufacture of cultured tissues and cells,
- reduced user handling during culture of cultured cells and tissues,
- reduced contamination of cultured tissues and cells, or
- reduced cell or tissue loss and/or increased yield during cell or tissue culture.

1. Definitions

The term "and/or" can mean "and" or "or".

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The term "gas-liquid interface" or "air-liquid interface" as used in this specification means a surface at which proliferating or differentiating cells or tissues are in contact with air or gas and a liquid simultaneously. An air-liquid interface is required for the growth of some cells and tissues. For example, an air-liquid interface is required for the growth of full thickness dermal skin, whereby the dermal layer of the growing skin is in contact with liquid cell culture media and the epidermal layer is in contact with air in order to induce epidermal stratification. For some cells or tissue types the high oxygen culture conditions at or adjacent an air-liquid interface or gas-liquid interface promote cell growth, differentiation or stratification, and/or the formation of multicellular layers or multilayer tissues.

The term "gas permeable interface" as used in this specification means a surface located between a gaseous environment and a closed environment that allows gas exchange to occur but is liquidly sealed. The one or more gas permeable interfaces present in the apparatus described herein provide an interface that promotes cell or tissue proliferation, differentiation and/or stratification in a similar manner to an air-liquid or gas-liquid interface. In particular, the one or more gas permeable interfaces present in the apparatus described herein provide an interface that promotes epithelial cell, for example, keratinocyte proliferation and differentiation and/or epithelial or epidermal stratification.

The term "gas permeable material" as used in this specification means a material through which gas exchange may occur. Gas permeable membranes are particularly contemplated for use in the apparatus described herein.

The term "in gaseous communication" as used in this specification with reference to the interaction between a scaffold of an apparatus of the invention and a gas permeable material, or a substrate, cells or tissue disposed on a substrate and a gas permeable material, means that the scaffold, substrate, cells or tissue are in sufficient proximity to the gas permeable material to allow gas exchange between the environment and the substrate or cells (for example, a substrate or cells disposed on a scaffold) to occur in order to deliver, for example, increased oxygen to the substrate, cells or tissue. In some embodiments the scaffold, substrate or cells is in direct contact with the gas permeable material. In other embodiments the scaffold, substrate or cells is not in direct contact with the gas permeable material. For example, in various embodiments the scaffold, substrate or cells is maintained at a distance of less than about 0.01, 0.025, 0.05, 0.1, 0.25, 0.5, 0.75, 1, 1.5, 2, 2.5, 3, 3.5, 4, 4.5, 5, 5.5, 6, 6.5, 7, 7.5, 8, 9 or about 10 mm, and useful ranges may be selected from between any of these values, for example, from about 0 to about 10 mm, about 0 to about 5 mm, about 0 to about 2 mm, about 0 to about 1 mm, about 0 to about 0.5 mm, about 0 to about 1 mm, about 0.1 to about 10 mm, about 0.1 to about 5 mm, about 0.5 to about 5 mm, or from about 2 to about 5 mm.

The term "(s)" following a noun contemplates the singular or plural form, or both.

The term "subject" is intended to refer to an animal, preferably a mammal, more preferably a human. Mammalian subjects include cats, dogs and horses. Other mammalian subjects include an agricultural animal, including a horse, a pig, a sheep, a goat, a cow, a deer, or a fowl, or a laboratory animal, including a monkey, a rat, a mouse, a rabbit or a guinea pig.

The term "treat" and its derivatives should be interpreted in their broadest possible context. The term should not be taken to imply that a subject is treated until total recovery. Accordingly, "treat" broadly includes maintaining a subject's disease progression, symptoms or burn or wound healing at a substantially static level, increasing a subject's rate of recovery, amelioration and/or prevention of the onset of the symptoms or severity of a particular condition, burn, wound or other injury, or extending a patient's quality of life. The term "treat" also broadly includes the maintenance of good health for sensitive individuals and building stamina for disease, infection or infestation prevention.

2. Apparatus

The apparatus of the invention provides for the culture or engineering of cells and/or tissues that require or benefit from exposure to an air-liquid interface to stimulate or promote their growth, differentiation or stratification. The apparatus of the present invention provides for the culture of cells or tissues submerged in a liquid and in gaseous communication with a gas permeable surface.

A first embodiment of the apparatus is shown in FIG. 1. Apparatus 100 comprises a container 110 formed by first endwall 111 and at least one sidewall 112, and a detachable second endwall 120.

Container 110 is configured to sealingly engage with second endwall 120 to form a liquid seal. When engaged, container 110 and second endwall 120 define a chamber 130.

In one embodiment of the invention as shown in FIG. 1, a flange 114 extends laterally from container 110 at or towards end 113. In one embodiment flange 114 defines a groove 115 configured to retain an O-ring (not shown), for example, a rubber O-ring. The O-ring forms a liquid seal when the container engages with second endwall 120.

In one embodiment second endwall 120 is fastened to container 110. For example, second endwall 120 is fastened to container 110 using nuts and bolts.

In various embodiments second endwall 120 is configured to engage with container 110 by friction fit, a threading arrangement or one or more clamps.

In one embodiment a sidewall 112 or second endwall 120 comprises at least one fluidly-sealable access port 117. In one embodiment the apparatus further comprises a bung, such as a bung, or other member that engages with port 117 to form a liquid seal. For example, in one embodiment the apparatus comprises a rubber bung (not shown) that engages with port 117 to form a liquid seal, wherein a needle may be inserted through the rubber bung to inject cells or culture medium into the chamber. When the needle is removed, the liquid seal is restored.

In one embodiment container 110 and/or second endwall 120 are formed substantially of polycarbonate. Suitable materials for use in forming container 110 and/or second endwall 120 are materials that are sterilisable, for example, materials that are autoclavable or that may be irradiated.

At least a part of two or more of second endwall 120, endwall 111 and the at least one sidewall 112 comprise or is configured to engage with a gas permeable material. In an exemplary embodiment at least a part of first endwall 111 and second endwall 120 comprise or are configured to engage with a gas permeable material.

In one embodiment the gas permeable material is located on the interior surface of the endwall or sidewall. In one embodiment the gas permeable material is attached using an adhesive.

The part of second endwall 120, first endwall 111 and/or sidewalls 112 that comprises or engages with the gas permeable material is perforated to allow gaseous exchange as shown in FIG. 1. In one embodiment the part of the second endwall, first endwall and/or sidewall that comprises or engages with the gas permeable material comprises a plurality of perforations 140. In an exemplary embodiment perforations 140 are about 3 mm in diameter. In one embodiment the perforations extend to substantially the same area as the gas permeable material, thereby forming a gas permeable interface on the interior surface of each of endwalls 120 and 111.

In one embodiment, a flange extends from first endwall 111 and/or second endwall 120, the flange configured such that when apparatus 100 is placed on an external surface, the exterior face of first endwall 111 and/or second endwall 120 does not contact the external surface. The presence of one or more flanges in the apparatus may enhance gas exchange between the exterior environment and the chamber of the apparatus through perforations 140 and the gas permeable material.

In one embodiment, when apparatus 100 is in use and a gas permeable material is present and extended to entirely cover perforations 140, chamber 130 is liquidly sealable from but in gaseous communication with the environment.

In one embodiment the gas permeable material is a gas permeable membrane.

In various embodiments the gas permeable material has a thickness of less than about 50, 75, 100, 120, 125, 140, 145, 150, 155, 160, 170, 175, 200, 225, 250, 300, 350, 400, 450 or less than about 500 µm, and useful ranges may be selected from between any of these values, for example, from about 50 to about 500 µm, from about 100 to about 200 µm, or from about 125 to about 175 µm.

In one embodiment the gas permeable material is polydimethylsiloxane, silicone, fluoroethylenepolypropylene, polyolefin, or ethylene vinyl acetate copolymer.

It will be appreciated that properties including the degree of the gas permeability, moisture vapour transmission, biocompatibility with cells, and physical strength or integrity are important considerations for the selection of a suitable gas permeable material for use in the apparatus.

Apparatus 100 further comprises a scaffold 150 located in chamber 130 that is adapted to receive a substrate for cells to reside upon. In one embodiment scaffold 150 is detachable from the apparatus.

In one embodiment scaffold 150 is oriented substantially parallel with first endwall 111 and/or second endwall 120.

In one embodiment scaffold 150 is substantially planar and may be in the form of a frame adapted to retain a substrate. In one embodiment the scaffold comprises a clamp or clip that retains the substrate in or on the scaffold under tension.

In one embodiment the substrate is directly bound or applied to scaffold 150.

In one embodiment the apparatus comprises a plurality of scaffolds wherein each scaffold comprises a discrete substrate. In one embodiment each scaffold comprises a different substrate. In one embodiment each scaffold comprises the same substrate.

In another embodiment the scaffold comprises a plurality of separated substrates. In one embodiment the separated substrates are the same substrate. In another embodiment the separated substrates are different substrates.

In an alternative embodiment a member comprising the substrate is fitted to scaffold 150, for example by adhesive, clamping or friction fit.

Scaffold 150 is configured to engage with one or more sidewalls 112 to allow substantially linear movement of scaffold 150 between a first position at or towards first endwall 111 and a second position at or towards second endwall 120, or vice versa, when, in use, apparatus 100 is inverted. In either the first position or the second position, or both the first position and the second position, the substrate is in gaseous communication with the gas permeable material. In one embodiment the substrate is in contact with the gas permeable material.

For example, in use, when apparatus 100 is oriented in a first mode so that first endwall 111 is at the bottom and second endwall 120 is at the top of the apparatus, scaffold 150 is located in a first position at or towards first endwall 111. When apparatus 100, in a second mode, is inverted so that first endwall 111 is at the top, scaffold 150 moves linearly by force of gravity to a second position at or towards second endwall 120.

Scaffold 150 is configured to engage with the one or more sidewalls 112 such that rotation or inversion of the scaffold about an axis perpendicular to at least one sidewall 112 is restricted.

In one embodiment, scaffold 150 has one or more lugs that engage with one or more complementary grooves in the at least one sidewall 112 to allow translational movement of scaffold 150 but to restrict rotational movement. In an alternative embodiment the at least one sidewall 112 has one or more lugs that engage with one or more complementary grooves in scaffold 150.

In one embodiment scaffold 150 is formed from stainless steel. It will be appreciated that other suitable materials include materials of sufficient density that when chamber 130 is filled with a volume of liquid and the apparatus is inverted, scaffold 150 moves through the liquid from the first position to the second position. Suitable materials to form the scaffold include materials that are biocompatible and resistant to oxidation or degradation caused by tissue culture media.

In one embodiment scaffold 150 comprises one or more apertures to allow movement of liquid in chamber 130 and to release trapped air when apparatus 100 is inverted.

It will be appreciated that other systems to guide translational movement but restrict rotational movement of scaffold 150 may be used.

Figure 2:
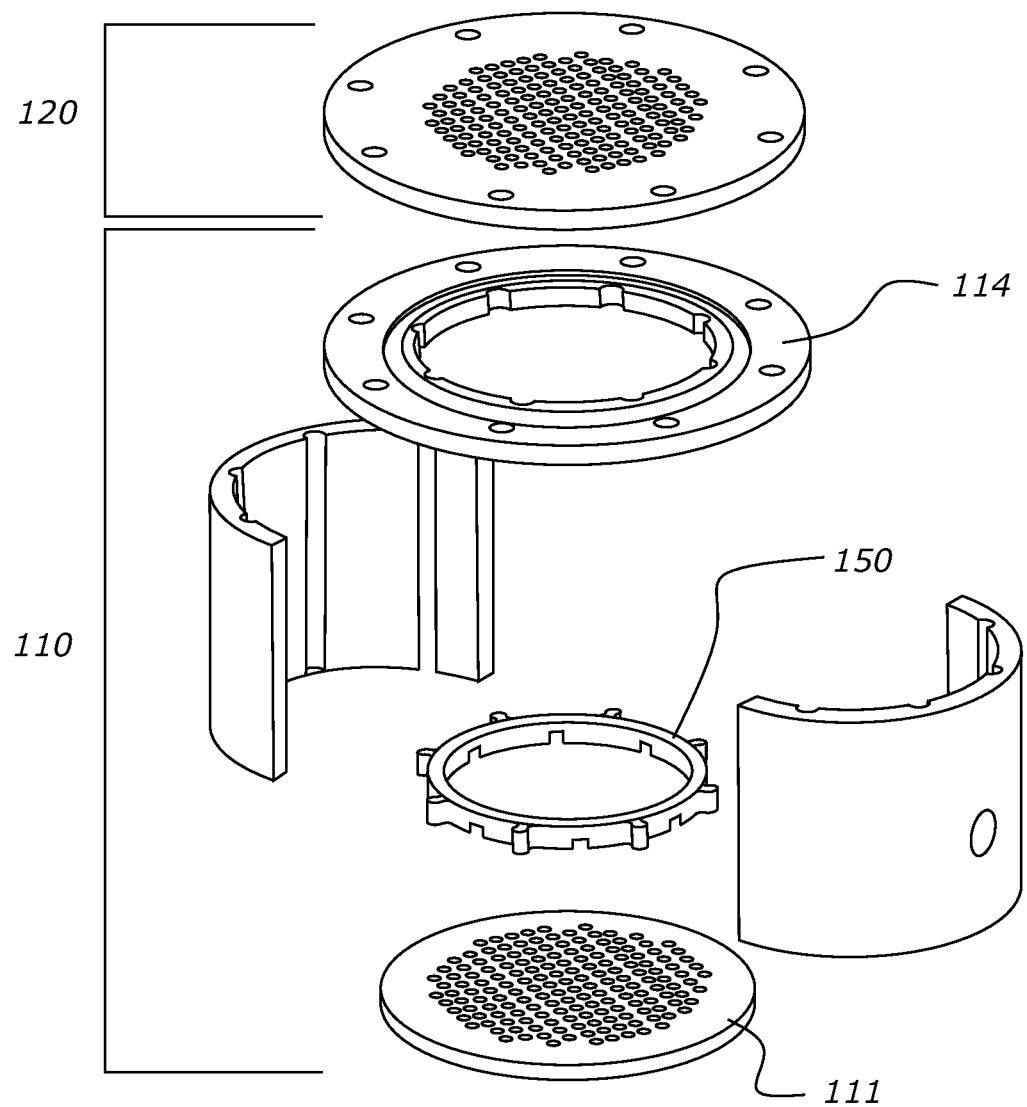
FIG. 2 is an exploded perspective view of the apparatus shown in FIG. 1.

In an alternative embodiment container 110 is cylindrical as shown in FIG. 2. In this embodiment first endwall 111, second endwall 120, flange 114 and/or scaffold 150 may also be circular in shape.

Figure 3:
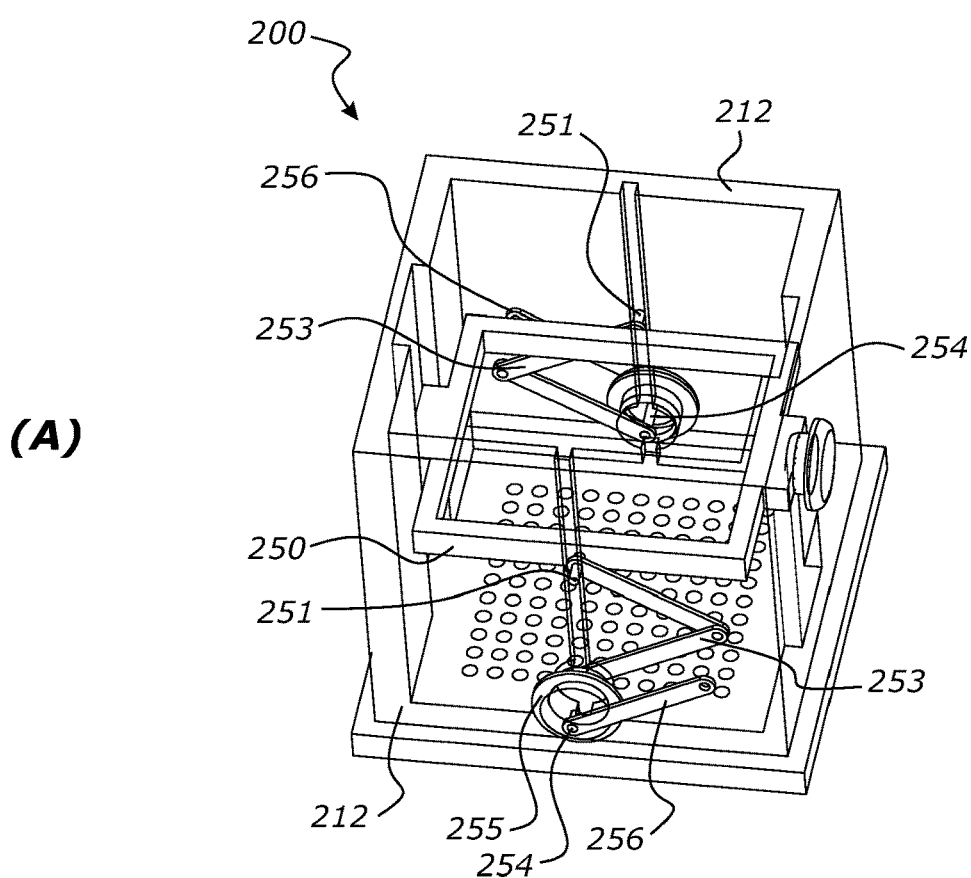
FIG. 3 is a perspective view of a second embodiment of the apparatus showing movement of the scaffold between A) a first position and B) a second position.
Figure 3:
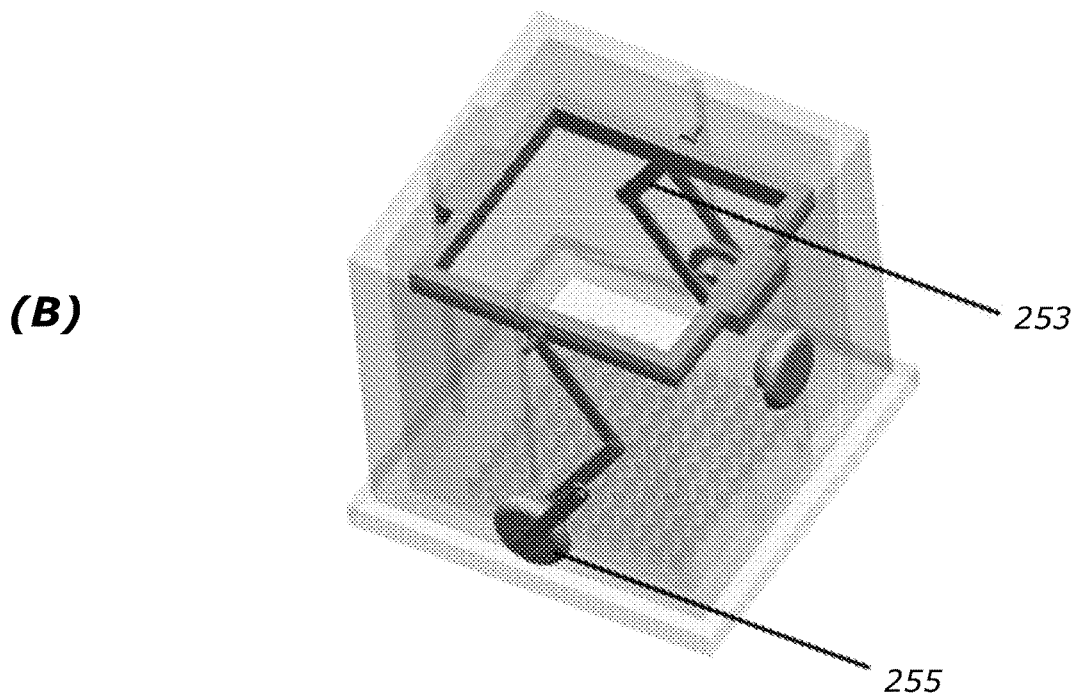
Figure 3:
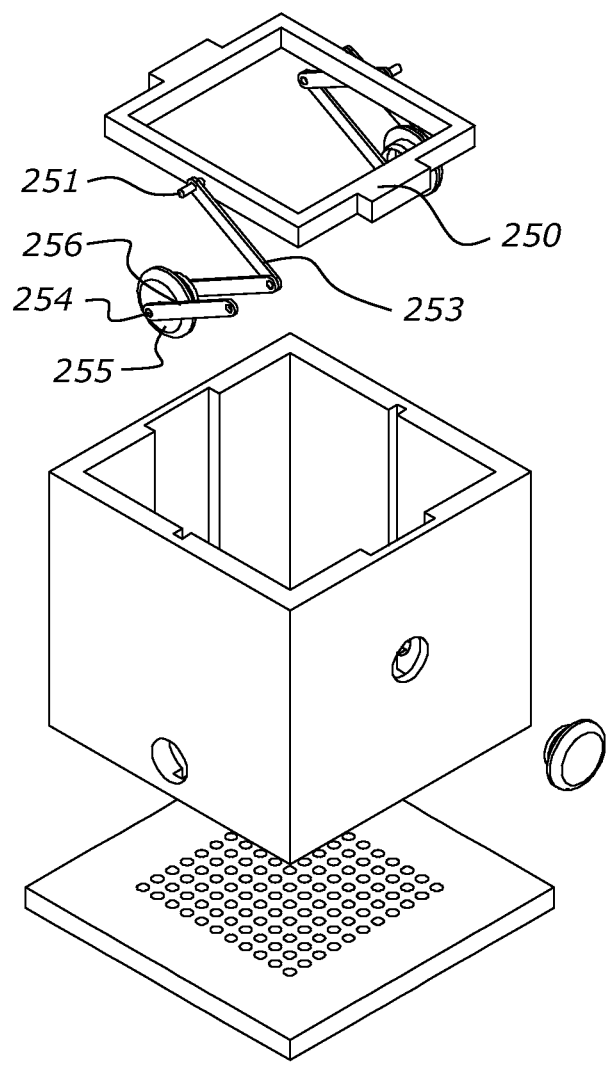

A second embodiment of the apparatus is shown in FIG. 3 comprising an alternative system to guide translational movement but restrict rotational movement of the scaffold.

Apparatus 200 comprises a scaffold 250 operated by a double arm lever to achieve substantially linear movement between first and second positions.

In this embodiment scaffold 250 is in the form of a frame fixedly attached, or integral with, pins 251 extending from opposing sides of scaffold 250 towards sidewalls 212. Hinged levers 253 moveably engage with pins 251 and extend in opposing orientations to fixedly engage with pins 254 that extend through sidewalls 212.

In one embodiment apparatus 200 comprises one or more bungs 255 that sealably engage with the apertures in sidewalls 212 housing pins 254.

Apparatus 200 further comprises one or more opposing handles 256 located on the exterior of opposing sidewalls 212 and fixedly engaged with pins 254. In embodiments comprising more than one handle, conveniently the handles 256 extend in opposing directions.

Translational, linear movement of scaffold 250 from a first position shown in part A of FIG. 3 is achieved by rotating one or both handles 256 about an axis perpendicular to sidewalls 212 to drive hinged levers 253 to open and raise scaffold 250 to the second position shown in part B of FIG. 3.

Figure 4:
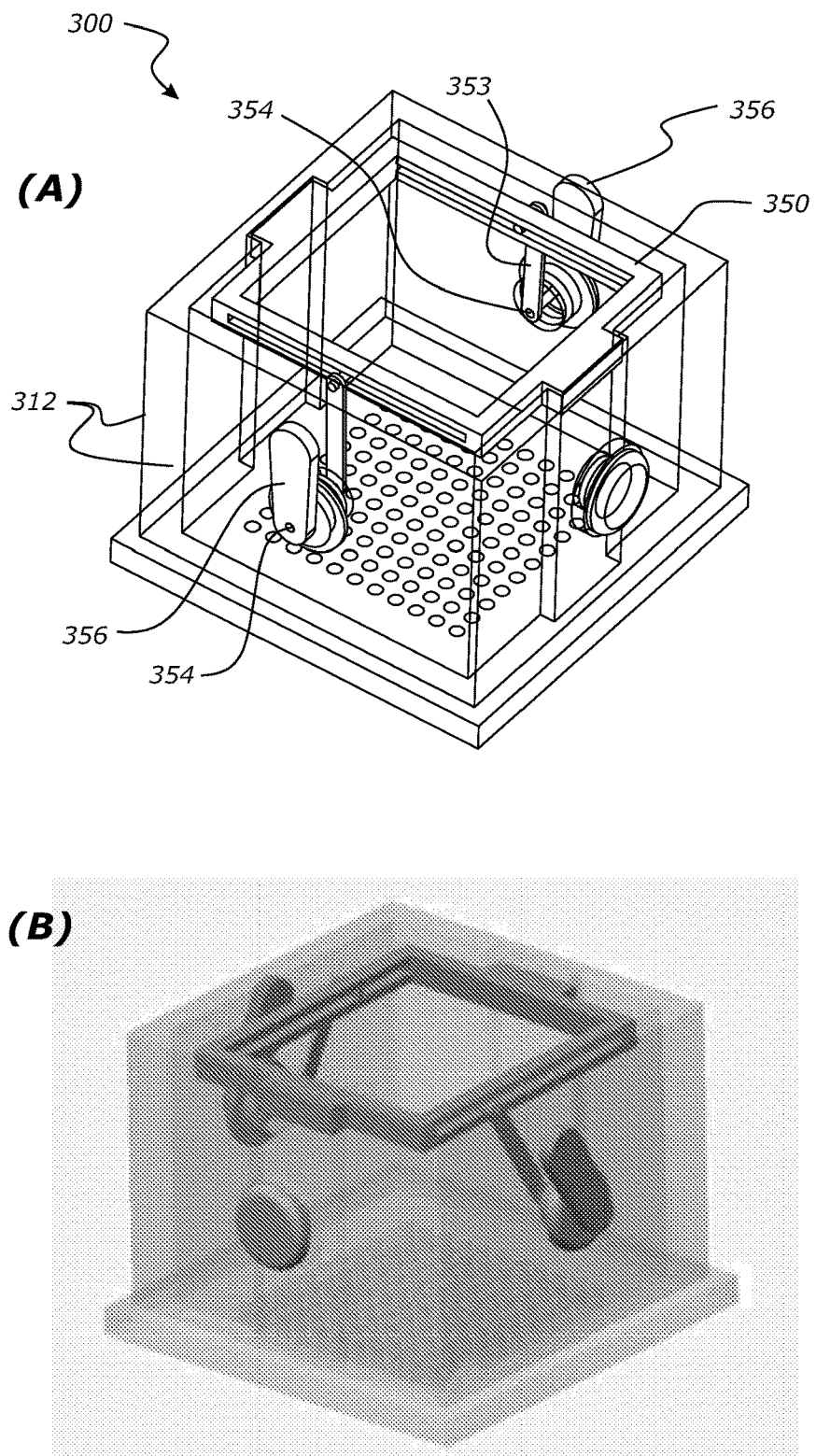
FIG. 4 is a perspective view of a third embodiment of the apparatus showing views from A) a first perspective and B) a second perspective.
Figure 4:
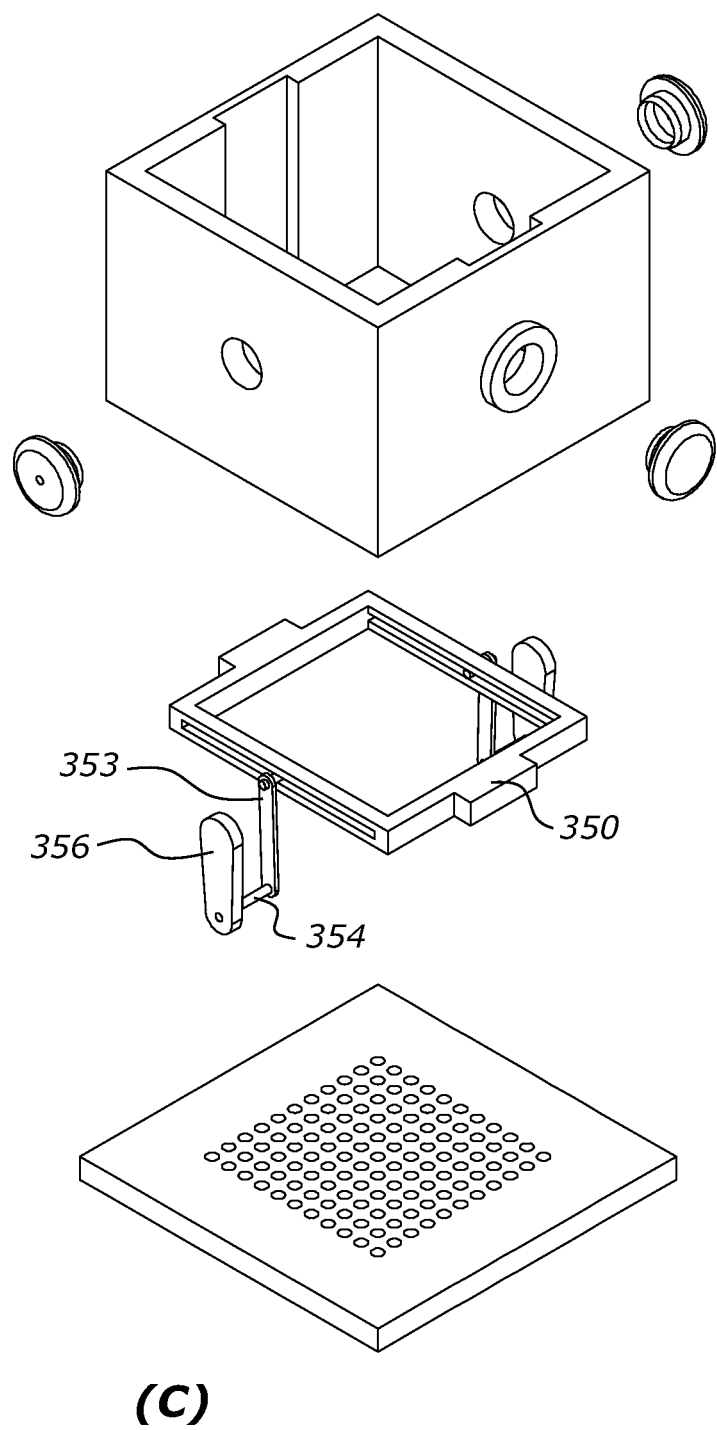

A third embodiment of the apparatus is shown in FIG. 4 comprising a further alternative system to guide translational movement but restrict rotational movement of the scaffold.

In this embodiment scaffold 350 moveably engages with lever arms 353 extending from opposing sides of scaffold 350 towards sidewalls 312. Lever arms 353 engage with scaffold 350 at or towards opposing corners of scaffold 350.

Lever arms 353 extend in opposing orientations to fixedly engage with pins 354 that extend through sidewalls 312.

Apparatus 300 comprises one or more opposing handles 356 located on the exterior of opposing sidewalls 312 and fixedly engaged with pins 354. In embodiments comprising more than one handle, conveniently the handles 356 extend in opposing directions.

Translational, linear movement of scaffold 350 from a first position to a second position is achieved by rotating one or both handles 356 about an axis perpendicular to sidewalls 312 to force lever arms 352 to open and raise or lower scaffold 350.

Figure 5:
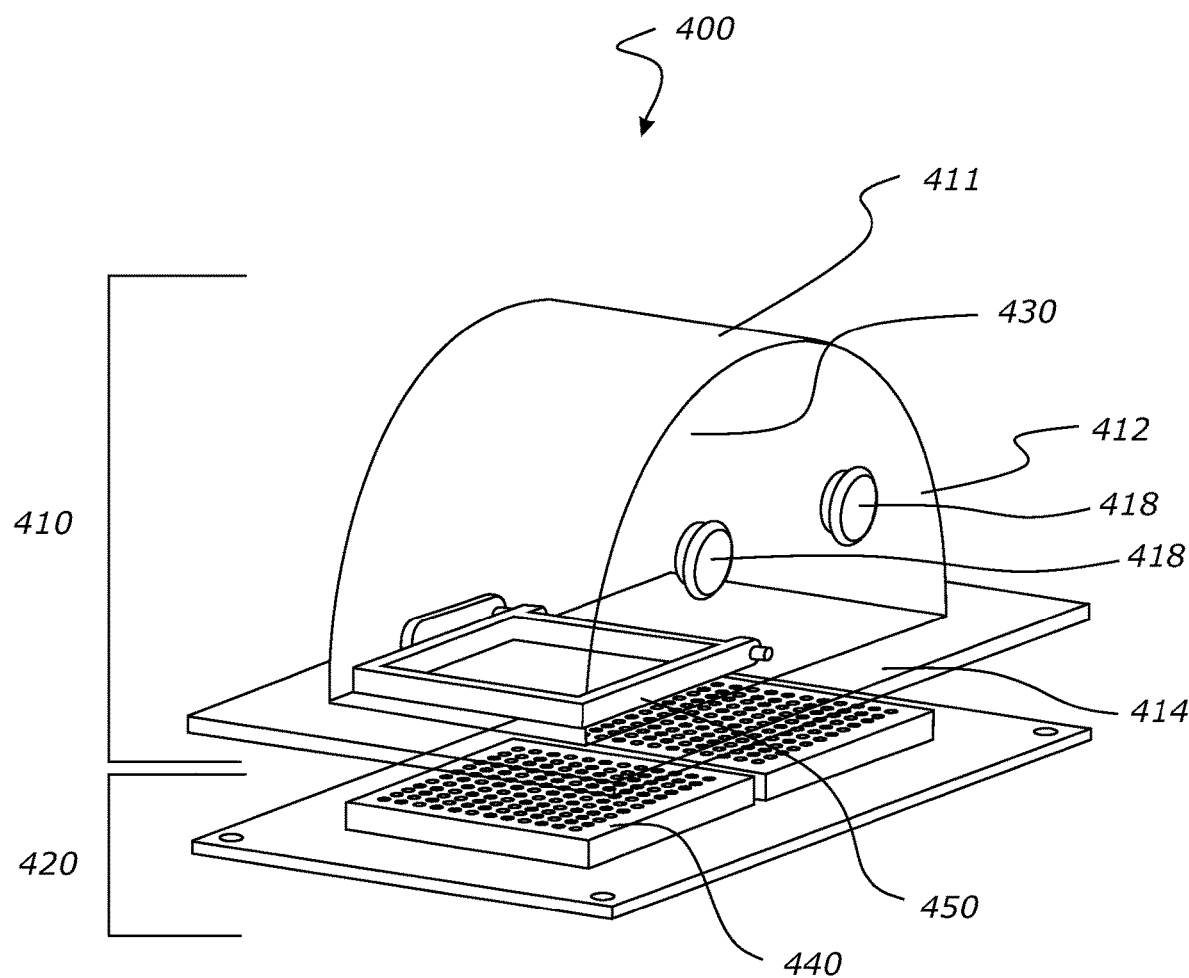
FIG. 5 is an exploded perspective view of a fourth embodiment of the apparatus.

A fourth embodiment of the apparatus is shown in FIG. 5.

Apparatus 400 comprises a container 410 formed by first endwall 411 and sidewalls 412, and a second endwall 420.

Container 410 is configured to sealingly engage with second endwall 420 to form a liquid seal and define a chamber 430. Apparatus 400 may comprise a flange 414 and sealing arrangement as described above for apparatus 100.

In one embodiment at least one sidewall 412 comprises at least one fluidly-sealable access port. In one embodiment the apparatus further comprises a bung 418 or other member that engages with the port to form a liquid seal.

At least a part of second endwall 420 comprises or is configured to engage with a gas permeable material. In one embodiment two or more separated regions of second endwall 420 comprise or are configured to engage with a gas permeable material as shown in FIG. 4.

The one or more regions of second endwall 420 that comprise or engage with the gas permeable material are perforated to allow gaseous exchange as described for apparatus 100. In one embodiment the one or more regions of the second endwall that comprise or engage with the gas permeable material comprises a plurality of perforations 440.

In one embodiment, when apparatus 400 is in use and a gas permeable material is present and extended to entirely cover both regions comprising perforations 440, chamber 430 is liquidly sealable from but in gaseous communication with the environment.

Apparatus 400 further comprises a scaffold 450 located in chamber 430 that is adapted to receive a substrate for cells to reside upon. The substrate may be applied or fitted to scaffold 450 as described above for apparatus 400.

In one embodiment scaffold 450 is detachable. In another embodiment scaffold 450 is fixed to apparatus 400.

Scaffold 450 is configured to engage with one or both sidewalls 412 to allow substantially rotational movement of scaffold 450 about an axis perpendicular to one or both sidewalls 412.

Figure 6A:
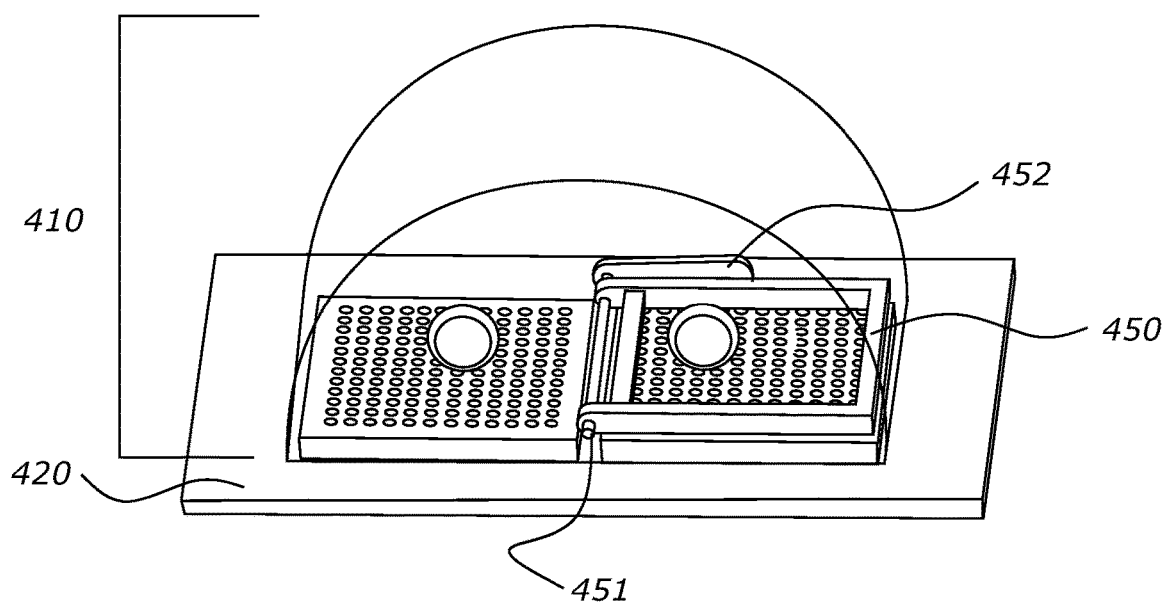
FIG. 6 is a perspective view of the apparatus shown in FIG. 5 showing movement of the scaffold between A) a first position and B) a second position.
Figure 6B:
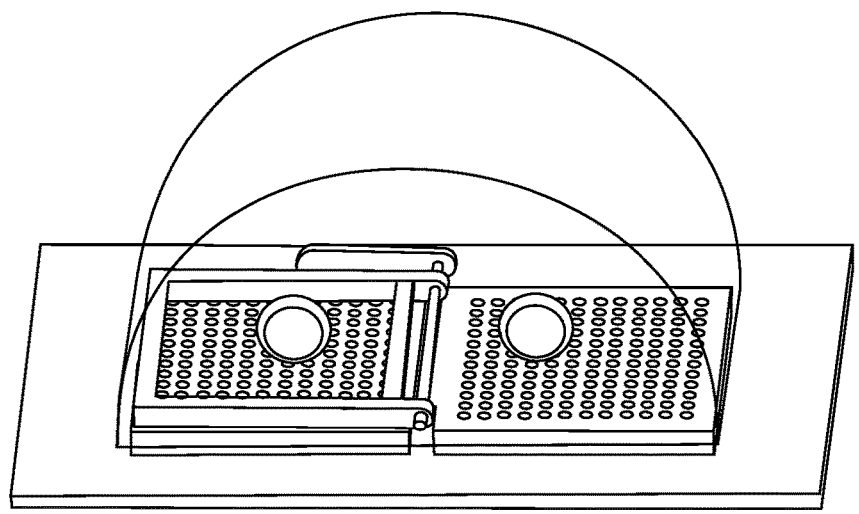

Movement of scaffold 450 is shown in FIG. 6.

In one embodiment scaffold 450 engages with a pin 451 that extends across the width of chamber 430 between sidewalls 412.

In one embodiment scaffold 450 is fixedly attached to pin 451. Pin 451 rotates freely about an axis perpendicular to one or both sidewalls 412. In this embodiment the apparatus comprises a handle 452 located on the exterior of container 410 and fixedly attached to an end of pin 451. In one embodiment the apparatus comprises a second handle extending from the opposing end of pin 451.

Scaffold 450 moves between a first position shown in part A of FIG. 6 and a second position shown in part B of FIG. 6. In the first position a side of scaffold 450 contacts a first region of endwall 420. In an embodiment wherein the first region of endwall 420 comprises a gas permeable material, the substrate is in gaseous communication with or directly contacts the gas permeable material in the first position.

A user moves scaffold 450 by rotating handle 452 about pin 451 to move scaffold 450 to the second position so that the opposing planar surface of scaffold 450 contacts a second region of endwall 420. In an embodiment wherein the second region of endwall 420 comprises a gas permeable material, the substrate is in gaseous communication with, or contacts, the gas permeable material in the second position.

It will be appreciated that other systems to guide rotational movement of scaffold 450 may be used.

In one embodiment apparatus 400 comprises a partition (not shown) extending from the interior surface of first endwall 411 towards second endwall 420 and extending between sidewalls 412 to bisect chamber 430 and form two sub chambers. The partition is configured so as to not obstruct rotational movement of scaffold 450. In one embodiment pin 451 may be housed within the partition.

Culture media may be added to one or both subchambers. Addition of culture media to one subchamber provides an adequate volume of media for the growth and differentiation of cells or tissue located in the subchamber, while providing a large gaseous volume of the chamber, thus maximising gas exchange at the interface between the media and the gas in the chamber.

In one embodiment one or more of the sidewalls of the container are deformable. In this embodiment manual manipulation of the deformable sidewalls is used to effect or allow translational movement of the scaffold at least partway between the first and second endwalls of the container.

In one embodiment the apparatus comprises a removable or dissolvable cover at least partially covering the gas permeable material. The cover may be removed by a user to allow media, cells, tissue or the substrate to come into contact with the gas permeable material.

In one embodiment the removable cover comprises a dissolvable material. The cover is dissolved when liquid is added to the chamber of the apparatus.

Figure 7:
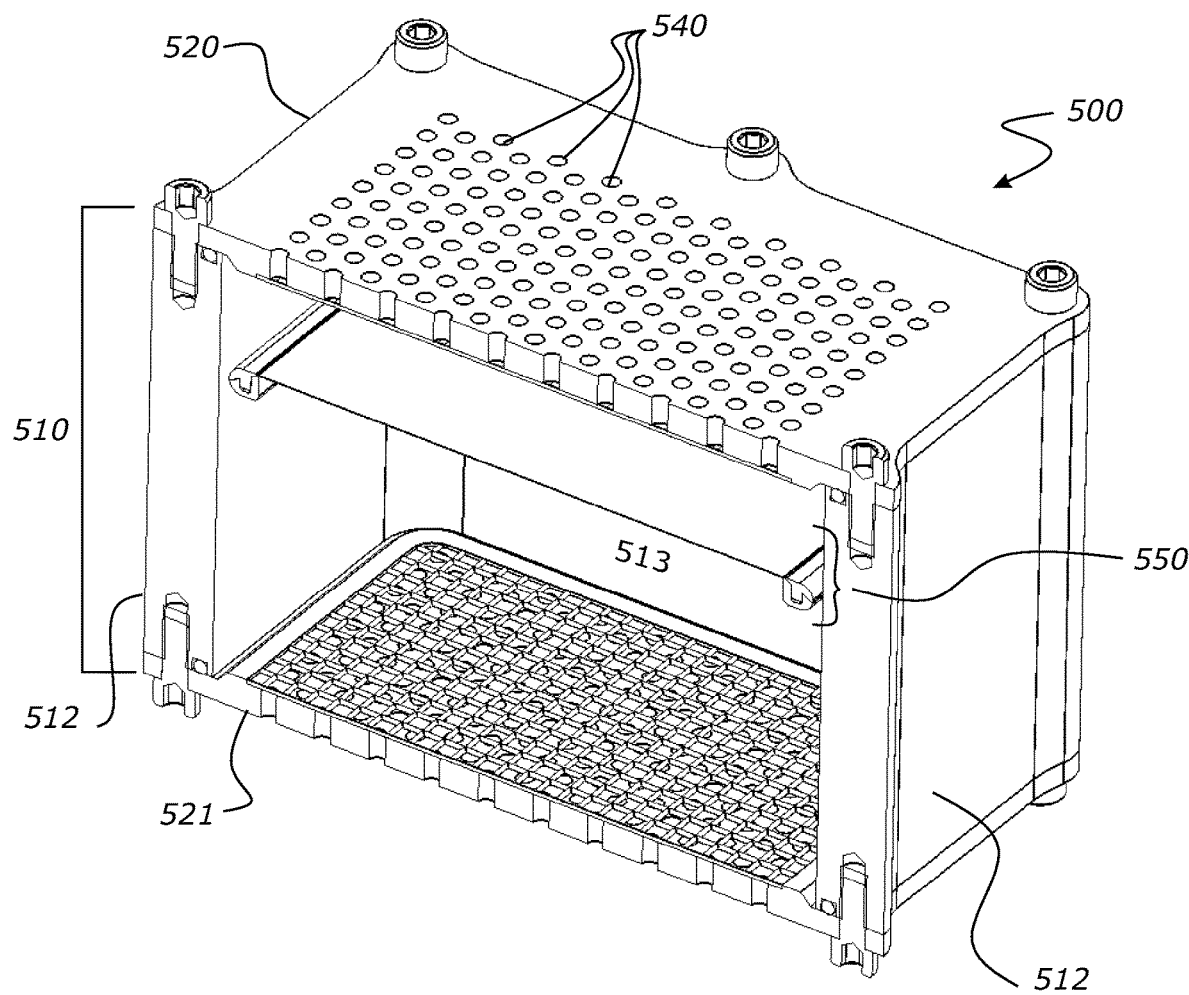
FIG. 7 shows an upper front perspective view of a fifth embodiment of the apparatus with a cross section taken through the apparatus in the plane of back wall 513.

A fifth embodiment of the apparatus is shown in FIG. 7.

Apparatus 500 comprises a body 510 formed by sidewalls 512, back wall 513, a front wall (not shown), and opposing detachable endwalls 520 and 521.

In one embodiment body 510 is configured to sealingly engage with endwalls 520 and 521 to form a liquid seal. In one embodiment the liquid seal is formed when endwalls 520 and 521 are fastened to body 510 using screws. Other suitable fastening means that may be used will be apparent to those skilled in the art, including those discussed above.

When engaged, body 510 and endwalls 520 and 521 define a chamber.

In one embodiment any wall of body 510 comprises at least one fluidly-sealable access port 517. In one embodiment a bung or other member that engages with access port 517 is used to form a liquid seal as described above.

Endwalls 520 and 521 comprise a plurality of perforations 540 as shown in FIG. 7 to allow gaseous exchange between the chamber and the environment. At least a part of endwalls 520 and 521 is configured to engage with a gas permeable material (not shown) that extends to entirely cover perforations 540 such that, when apparatus 500 is in use, the chamber is liquidly sealed from, but in gaseous communication with, the environment. A gas permeable interface (GPI) is thereby formed on the interior surface of each of endwalls 520 and 521.

In use, the GPIs provide for gas diffusion into media within the apparatus and promote cell or tissue proliferation, differentiation and/or stratification when cells seeded on the substrate are in direct contact with a GPI.

Apparatus 500 comprises a scaffold 550 located in the chamber that is adapted to receive a substrate 551.

Figure 8:
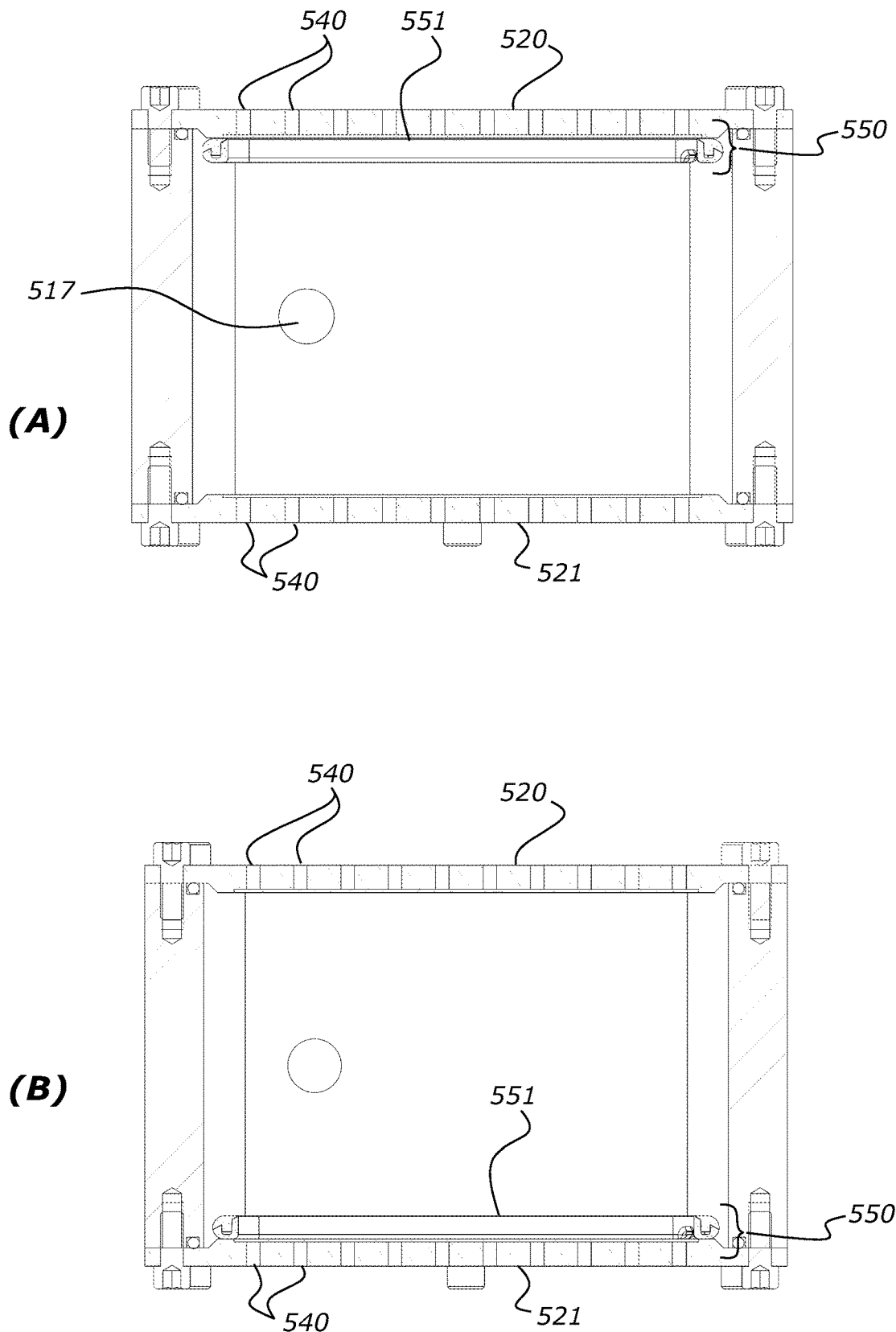
FIG. 8 shows a front view of the embodiment shown in FIG. 7 showing the scaffold in A) a first position and B) a second position.

As shown in FIG. 8, scaffold 550 is configured to engage with one or more sidewalls 512 to allow substantially linear translational movement of scaffold 550 between a first position (A) at or towards endwall 520 and a second position (B) at or towards endwall 521. In use, scaffold 550 moves between the first and second positions when apparatus 500 is inverted.

In one embodiment the dimensions of the apparatus 500 and scaffold 550 are such that the scaffold is greater in one dimension (width or length) than the apparatus is deep. These dimensions ensure smooth linear transitional movement of scaffold 550 between the first and second positions while restricting rotational movement to avoid buckling or jamming of scaffold 550 in the apparatus.

It will be appreciated that other systems to guide transitional movement of the scaffold but restrict rotational movement may be used, including the systems described above.

In use, when scaffold 500 is in the first position shown in FIG. 8A, the upper surface of substrate 551 is in contact with the GPI on the interior surface of endwall 520.

In use, when scaffold 550 is in the second position shown in FIG. 8B, the lower surface of substrate 551 is in close proximity to, but not in direct contact with, the GPI on the interior surface of endwall 521.

In use, cells or tissues that require contact with a GPI in order to proliferate, differentiate or stratify, such as keratinocytes, should be seeded on the upper surface of substrate 551. In other words, the cell or tissue should be added to the apparatus when scaffold 550 is in the second position shown in FIG. 8B.

In an alternative embodiment (not shown), a part of endwall 521 is raised to form a platform that engages the gas permeable material. In this embodiment the platform is configured such that, in use, the lower surface of substrate 551 contacts the GPI at endwall 521 when scaffold 550 is in the second position. In this embodiment, apparatus 500 can be manipulated in use such that the upper surface of substrate 551 contacts a GPI in the first position and the lower surface contacts a GPI in the second position.

In use, cells added to the chamber adhere to the substrate 551. Cells may adhere to the upper surface of substrate 551, the lower surface of substrate 551 or both the upper and lower surfaces of substrate 551.

Figure 9:
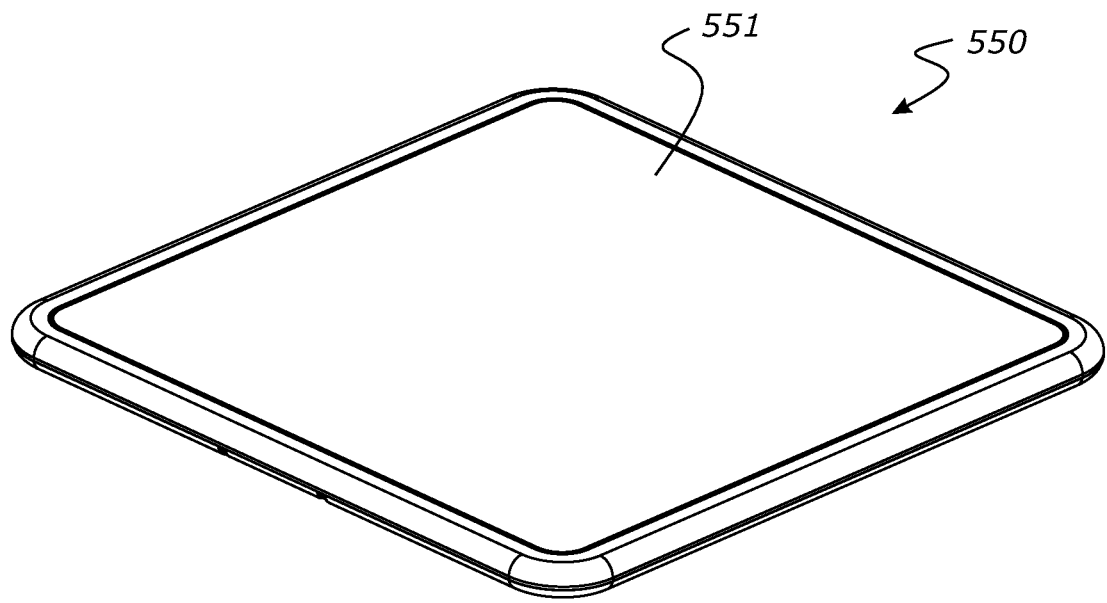
FIG. 9 shows a top perspective view of the scaffold of the embodiment of FIG. 7 showing the scaffold engaging a substrate.

In one embodiment scaffold 550 is in the form of a frame as shown in FIG. 9. Scaffold 550 is configured to retain substrate 551 under tension. In a preferred embodiment substrate 551 covers substantially all of the top edge of scaffold 550.

Figure 10:
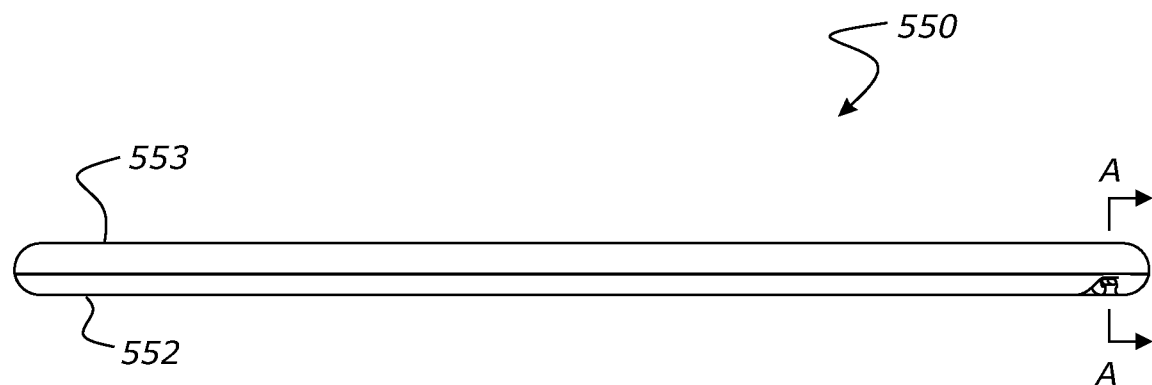
FIG. 10 shows a left view of the embodiment of FIG. 9.

In one embodiment the scaffold comprises a lower member 552 and an upper member 553 as shown in FIG. 10.

Figure 11:
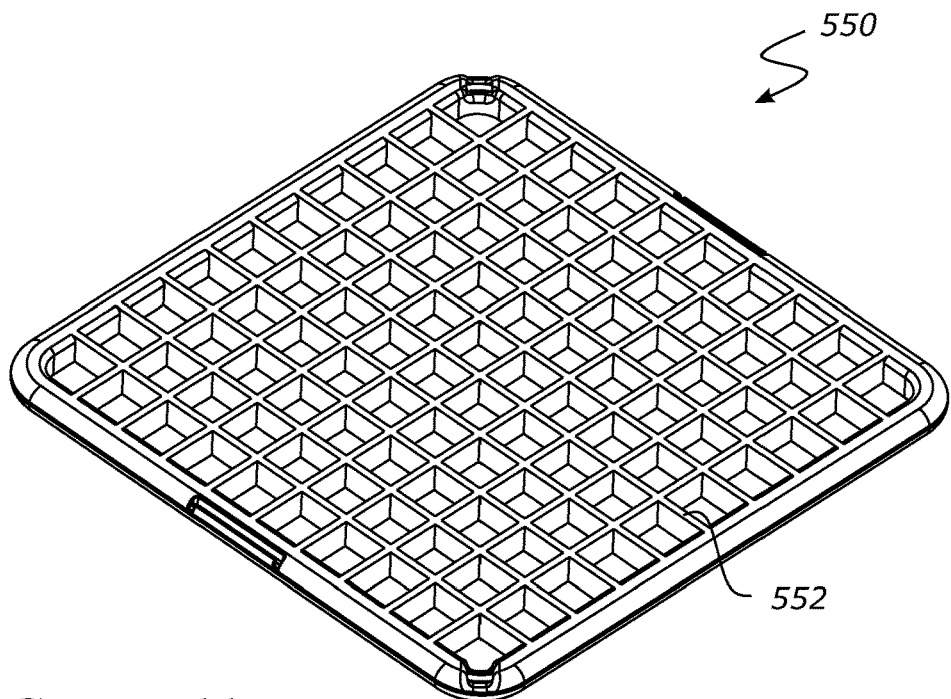
FIG. 11 shows a bottom perspective view of the embodiment of FIG. 9 without a substrate.

In one embodiment lower member 552 forms a grid as shown in FIG. 11 that supports the substrate and allows liquid and air to pass through the scaffold when the apparatus is inverted in use.

Figure 12:
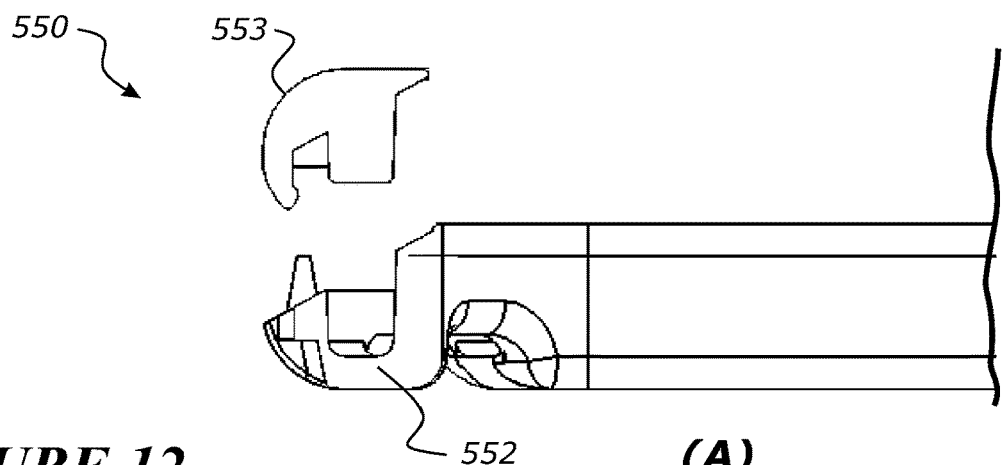
FIG. 12 shows A) a left exploded view of a cross section of the embodiment of FIG. 10 taken through plane A-A (no substrate); and (B) a left view of a cross section through plane A-A showing the scaffold engaging a substrate.

As shown in FIG. 12, in use, lower member 552 and upper member 553 are configured to retain a substrate on the scaffold. A substantially planar substrate 551 is placed across the top surface of lower member 552. Lower member 552 is shaped around its perimeter to engage upper member 553 to form a friction fit that retains substrate 551 under tension. In one embodiment lower member 552 and upper member 553 retain the substrate around the entire perimeter of scaffold 550.

In one embodiment scaffold 550 comprises one or more clips or clamping members to fixedly engage lower member 552 and upper member 553.

An alternative embodiment of lower member 552 is shown in FIG. 13. In this embodiment lower member 552 comprises one or more protrusions 5521 on its top surface. In use, hen upper member 553 is fitted over the substrate into lower member 552, protrusions 5521 pierce the substrate as shown in FIG. 14. Fixing the substrate to the scaffold this way may prevent contraction or displacement of the substrate in use.

Figure 15:
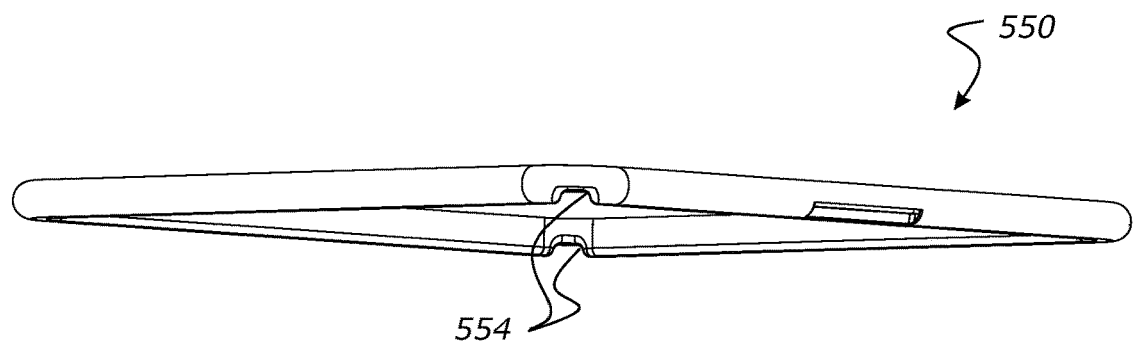
FIG. 15 shows a view highlighting the trapped air release mechanism of the embodiment of FIG. 9.

In one embodiment scaffold 550 comprises one or more apertures 554 as shown in FIG. 15 that allow air trapped under the substrate to pass through the scaffold. In one exemplary embodiment apertures 554 are located at two or more corners of scaffold 550.

Figure 16:
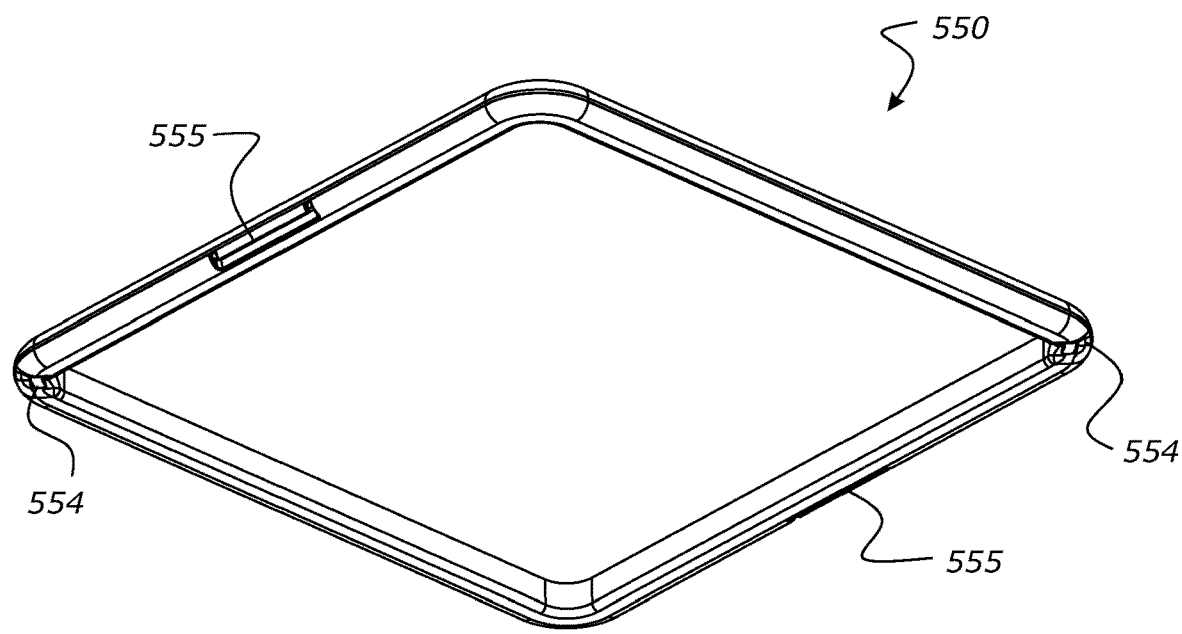
FIG. 16 shows a perspective view of the underside of the scaffold of FIG. 9.
Figure 17:
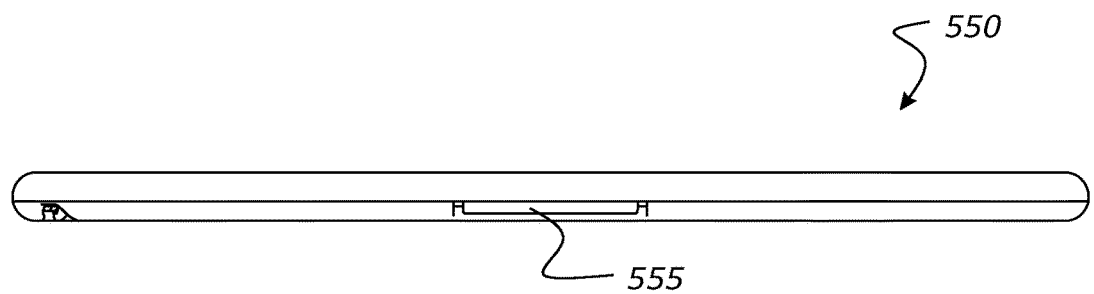
FIG. 17 shows a right view of the scaffold of FIG. 9.

In one embodiment scaffold 555 comprises one or more recesses 555 located at a position along the length of a side of the scaffold frame as shown in FIGS. 16 and 17. In use, a tool may be inserted in recess 555 to lever apart lower member 552 and upper member 553 to release the substrate from the scaffold.

3. Method

Culture or engineering of some cells and tissues benefits from or requires an oxygen-rich environment. This can be achieved by using culturing techniques that dispose the growing cells or tissue at an air-liquid interface. These techniques typically involve positioning the cells or tissue at the surface of the liquid tissue culture media in proximity to the gas present in the chamber of the tissue culture vessel. Such techniques are very difficult to implement precisely, particularly in order to grow tissues having a large area. Maintenance of these cultures over many weeks inevitably results in sub-optimal conditions for cell growth, due to the practical difficulty of maintaining a consistent depth of medium over all parts of the tissue. Multiple changes of the culture media is typically required which risks contamination of the cells or tissue.

The invention provides an efficient and precise method of culturing or engineering cells or tissues that require exposure to an air liquid interface, or that benefit from culture in a high oxygen environment.

The methods and apparatus described herein may be used to culture or engineer complex tissues from cells. The methods and apparatus provide an environment that promotes proliferation and differentiation of cells to form complex tissue structures.

In various embodiments the method is a method of culturing epithelial cells, for example, epidermal cells such as keratinocytes.

In various embodiments the method is a method of stimulating or maintaining epithelial cell proliferation or differentiation.

In various embodiments the method is a method of culturing one or more confluent layers of cells on a substrate, wherein said one or more confluent layers are disposed over at least part of the substrate. In one embodiment the method is a method of culturing cells in multicellular layers.

In one embodiment the method is a method of culturing tissue. In various embodiments the method is a method of culturing tissue comprising epithelial tissue (epithelium), stratified epithelial tissue, epidermal tissue (epidermis), stratified epidermal tissue, or stratified epidermal tissue and dermal tissue (dermis).

In one embodiment the method is a method of culturing epithelium. In various embodiments the method is a method of culturing a single cell-thick layer of keratinocytes, or stratified epithelium comprising at least two of the stratum basale, stratum spinosum, stratum granulosum, stratum lucidum and stratum corneum.

In a particularly contemplated embodiment the method is a method of culturing skin or skin tissue. In a particularly preferred embodiment the method is a method of culturing skin comprising dermal and epidermal layers or full thickness skin.

In various embodiments, cells, tissue, epithelium or skin are derived from humans or non-human animals. In one embodiment the cells, tissue, epithelium or skin are mammalian. In various embodiments the cells, tissue, epithelium or skin are human, monkey, rabbit, equine, porcine, ovine, murine, canine, feline, bovine, caprine, or avian.

In various embodiments the epithelial tissue (epithelium) comprises simple epithelium that is only one cell thick, stratified epithelium that is two or more layers thick, columnar epithelium, squamous epithelium, cuboidal epithelium, transitional epithelium or pseudostratified epithelium. In various embodiments the epithelium is keratinised or non-keratinised. In one embodiment the epithelium is ciliated. In one embodiment the epithelium comprises microvilli. In various embodiments the epithelium is simple columnar epithelium, stratified squamous epithelium, simple cuboidal epithelium or pseudostratified columnar epithelium. In various embodiments the epithelium is alveolar epithelium, endothelium, mesothelium, germinal epithelium, respiratory epithelium, corneal epithelium, olfactory epithelium, or urothelium.

In one aspect, the invention provides a method of culturing cells, the method comprising
  a) providing a suspension comprising cells to be cultured in an amount of tissue culture medium sufficient to support cell growth;
  b) introducing the suspension into a cell culture apparatus, wherein the apparatus comprises a container comprising a first endwall (bottom), at least one sidewall, and a detachable second endwall (top) adapted to engage with the container to define a chamber, and a scaffold adapted to receive a substrate for cells to reside upon, wherein at least a part of at least the first endwall (bottom), the at least one sidewall, or the second endwall (top) comprises a gas permeable material or is adapted to engage with a gas permeable material and is perforated to allow gaseous exchange; and wherein the apparatus is in a first mode in which the substrate is submerged in the suspension, and optionally is in contact with a gas permeable material,
  c) incubating the cell culture apparatus containing the suspension for a time sufficient for at least some of the cells to adhere to the substrate,
  d) adapting the cell culture apparatus to a second mode in which the substrate is disposed at a gas permeable material, and
  e) incubating the cell culture apparatus for a time sufficient
    i. for cell confluence to occur,
    ii. for cell differentiation to occur,
    iii. for cell proliferation to occur,
    iv. to form one or more confluent layers of cells, for example, one or more confluent layers of cells disposed over at least part of the substrate,
    v. to form stratified tissue, for example, stratified epidermal tissue, to occur,
    vi. for tissue growth to occur,
    vii. to allow migration of at least some cells, for example, fibroblasts, into or through the substrate, or
    viii. for a combination of any two or more of i) to v) to occur.

In one embodiment the suspension comprises a homogenous cell population. In one embodiment the suspension comprises a heterogenous cell population.

In one embodiment the suspension comprises cells obtained a tissue digest or partially purified tissue digest. For example, in one embodiment the suspension comprises cells obtained from a skin digest.

In various embodiments the cells are anchorage-dependent cells or adherent cells. In one embodiment the cells comprise keratinocytes, fibroblasts or keratinocytes and fibroblasts.

In various embodiments the cells comprise pigment-producing cells, vascular cells, pluripotent stem cells or immune cells. In one embodiment the cells comprise melanocytes, endothelial cells, smooth muscle cells, monocytes, macrophages, T lymphocytes, platelets, mast cells, adipose cells, or mesenchymal cells.

In one embodiment the tissue culture medium is Green's medium. In various embodiments the tissue culture medium comprises salts, growth factors, hormones and/or antibiotics. It will be appreciated that different tissue culture media may be appropriate for the growth of other cell or tissue types and/or different media additives may be used.

In various embodiments, the apparatus is an apparatus of the invention.

In one embodiment the cell suspension is introduced via an access port present in the chamber, for example, an access port present in the container. In another embodiment, the cell suspension is introduced to the container prior to attaching the second endwall (top).

In one embodiment, the substrate is biocompatible. In one embodiment, the substrate is biodegradable. In one embodiment, the substrate is impermeable to the cells. In another embodiment, the substrate is permeable to the cells. In one embodiment the substrate is gas permeable. In another embodiment the substrate is gas impermeable.

In various embodiments, the substrate is or comprises one or more of acellular de-epithelialised dermis (alloderm); dermis; collagen including collagen gel and tissues comprising collagen; tissue or cells of an epidermal or epithelial lineage, including tissues or cells from umbilical cord, placenta, mucosa, the digestive tract; fibronectin/fibrin; platelet rich plasma; Matrigel; components of and tissues comprising extracellular matrix including extracellular matrix secreted by cells such as fibroblasts; hyaluronic acid; electrospun biocompatible materials including PLGA; biocompatible polymers or combinations of biocompatible polymers, particularly those capable of being electrospun, including polyacrylic acid, poly L Lysine, collagen, gelatin, nylon, and polyesters; gelatine; peptide hydrogels; polyglactin scaffolds; dermagraft; elastin; chitosan; fibroin; spider silk; agarose, and any combinations of two or more thereof.

In an exemplary embodiment the substrate is or comprises poly(lactic co-glycolic acid) (PLGA). In a particularly preferred embodiment substrate is or comprises electrospun PLGA.

It will be appreciated that the cells and tissues recited above may be from any animal source, including human, equine, porcine, ovine, murine, canine, feline and bovine.

Those of skill in the art will, on reading the present disclosure, recognise that a substrate comprising one or more biologically derived products will generally provide appropriate stimulation for epidermal stratification to occur in certain embodiments of the invention without further modification, while substrates comprising one or more synthetic materials will typically require modification, such as a coating, to provide stimulus for epidermal stratification.

In one embodiment, the substrate comprises one or more molecules to aid cell adhesion or migration, differentiation, proliferation and/or stratification. For example, the substrate comprises one or more proteins, such as one or more basement membrane proteins, a collagen, a fibronectin, a laminin, or a lectin, one or more carbohydrates, such as one or more saccharides, or any combination of two or more thereof.

Suitable gas permeable materials for use in the method of the invention are discussed above. In various embodiments the gas permeable material is selected for optimal gas exchange, cellular growth, cell or tissue proliferation, tissue stratification and/or biocompatibility with the substrate, cells or tissue.

In one embodiment the substrate is disposed at a gas permeable material in the first mode. In one embodiment the substrate is disposed at a gas permeable material in the first mode and the second mode.

In one embodiment the method comprises the following additional steps between steps d) and e)

f) introducing a second suspension comprising cells to be cultured, for example via the access port, and g) incubating the cell culture apparatus containing the second suspension for a time sufficient for at least some of the cells in the second suspension to adhere to the substrate, and optionally h) adapting the cell culture apparatus to dispose the substrate or the cells at a gas permeable material.

It will be appreciated that incubation conditions commonly used in the art for cell or tissue culture may be used. For example, in one embodiment the apparatus is incubated at a temperature of about 37° C. in a humidified atmosphere comprising 5% carbon dioxide.

Full thickness skin comprising a dermal layer (dermis) and an epidermal layer (epidermis) may be formed using the methods described herein. Fibroblasts are added to the apparatus and cultured to form the dermis.

Keratinocytes added to the apparatus and cultured differentiate and proliferate to form a stratified epidermis. The applicant has observed that keratinocytes adhered to the substrate must directly contact the gas permeable interface for optimal epidermal stratification to occur.

In one embodiment fibroblasts and keratinocytes are introduced to the apparatus simultaneously.

In another embodiment fibroblasts and keratinocytes are introduced to the apparatus sequentially. For example, the method comprises introducing a first suspension comprising fibroblasts, incubating the apparatus for a time sufficient for the fibroblasts to adhere or to proliferate, or to form a dermis of a required thickness, then introducing a second suspension comprising keratinocytes. This embodiment may allow for the development of a thicker dermis.

In one embodiment the fibroblasts and keratinocytes are seeded on one surface of the substrate. In another embodiment fibroblasts are seeded on one surface of the substrate and keratinocytes are seeded on the opposing surface of the substrate.

In one embodiment the engineered tissue comprises the substrate. For example, fibroblasts may migrate into the substrate to form the the dermal layer of full thickness skin.

An exemplary embodiment of the method of the invention comprises the following steps.

A suspension comprising a heterogenous population of keratinocytes and fibroblasts is provided. The cells are provided in a volume of suitable tissue culture medium, for example, Green's medium, sufficient to support growth of the cells for a period of at least about 14 days.

An apparatus is provided comprising a scaffold comprising electrospun PLGA coated with collagen IV. The apparatus is provided in an orientation such that a first wall comprising a gas permeable material and having perforations is located at the top to form a gas permeable interface. The apparatus optionally comprises a gas permeable material located on the opposing second (bottom) wall, which is also perforated.

The scaffold is inserted into the apparatus such that the substrate side faces the bottom wall. When an apparatus such as that of the fifth embodiment described above is used, the scaffold is inserted in the apparatus so that the top surface of substrate 551 faces the first (top) wall.

The cell suspension is added to the apparatus and the apparatus is sealed. The apparatus is incubated for a period of about 48 hours to allow cell adherence to at least part of the surface of the substrate to occur.

The apparatus is inverted so that the scaffold moves to the opposing end (first wall) of the apparatus. The adhered cells are now in contact with the gas permeable interface at the top wall of the device. The apparatus is incubated for a period of about 14 days to induce production of a stratified epithelium. No further manipulation of the device is required.

After 14 days the scaffold comprises full thickness skin. The skin may be removed from the scaffold using a scalpel or other tool.

In a second exemplary embodiment fibroblasts and keratinocytes are added separately, and the apparatus is inverted twice.

An apparatus as described above for the first exemplary embodiment is used. The apparatus is provided in a first mode such that the substrate is in contact with the gas permeable material. A first cell suspension comprising a homogeneous population of fibroblasts is added to the apparatus. The apparatus is sealed and incubated for 48 hours.

After 48 hours the apparatus is inverted so that the scaffold moves to the opposing end of the device.

A second cell population comprising a homogenous population of keratinocytes is added, for example, using an access port on a sidewall of the apparatus. The apparatus is incubated for a period sufficient to achieve keratinocyte adherence, for example, about 48 hours.

The apparatus is inverted a second time so that the scaffold moves to the opposing end of the apparatus, and the keratinocytes are in contact with a gas permeable material. The apparatus is incubated for a period of about 14 days to induce production of a stratified epithelium.

It will be appreciated by those skilled in the art on reading this specification that particular embodiments of the above-mentioned methods provide advantages including eliminating the need to change culture media after seeding of cells in the apparatus or removing and transferring the developing tissue between culture vessels. Reducing the number of interventions required to produce, for example, full thickness skin, reduces the risk of contamination of the cells or tissues, and reduces the cost of production, a significant barrier to clinical implementation.

It will be appreciated that other methods of the invention achieve other advantages. Prior art methods of engineering full thickness skin require the use of an air-liquid interface (ALI). The disadvantage of such methods is that close monitoring of medium levels is required to maintain the growing tissue at the optimum ALI to achieve growth and epidermal stratification. The apparatus and methods of the invention provide for the growth, differentiation and/or engineering of cells or tissues using a gas permeable interface (GPI) that is not dependent on culture level and volume in the apparatus, which eliminates the need for careful monitoring during culture.

For example, a further method of the invention provides a method for culturing stratified epidermal tissue, or full thickness skin tissue, comprising the steps of:
 a) providing adhered cells or tissue disposed over at least a part of the surface of a substrate,
 b) introducing the adhered cells or tissue into a cell culture apparatus, wherein the apparatus comprises a container comprising a first endwall (bottom), at least one sidewall, and a detachable second endwall (top) adapted to engage with the container to define a chamber,
  wherein at least a part of the first endwall (bottom), the at least one sidewall, or the second endwall (top) comprises a gas permeable material or is adapted to engage with a gas permeable material and is perforated to allow gaseous exchange; and
  wherein the apparatus is in a first mode in which the substrate, adhered cells or tissue is submerged in the suspension and is in gaseous communication with a gas permeable material,
 c) incubating the cell culture apparatus containing the adhered cells or tissue for a time sufficient for epidermal stratification, or for the generation of full thickness skin, to occur.

For example, the adhered cells or tissue may be prepared by culturing keratinocytes, or fibroblasts and keratinocytes, on a de-epidermised dermis (DED) in a culture vessel. Once the cells have adhered, the cells disposed on the substrate are removed from the culture vessel and transferred to the apparatus.

The apparatus and methods of the invention are suitable for the culture and/or engineering of a range of epithelium or tissues comprising epithelial cells or tissue.

The apparatus and methods of the invention are particularly suitable for the culture of multicellular layers or multilayer tissues, which typically requires an oxygen-rich environment.

In particular, the methods and apparatus of the invention are suitable for the engineering of tissues or structures comprising simple epithelium, including simple squamous epithelium, simple cuboidal epithelium and simple columnar epithelium. stratified epithelium, including stratified squamous epithelium, stratified cuboidal epithelium and stratified columnar epithelium. Simple epithelium comprises a single layer of epithelial cells. Stratified epithelium comprises two or more layers of epithelial cells. The stratified epithelium may be keratinised or non-keratinised, or transitional epithelium. For example, the methods and apparatus of the invention are suitable for preparing epithelium including the outer layer of the skin (the epidermis), the cornea, the inner lining of structures of the gastrointestinal tract including the mouth, oesophagus, and rectum, the lining of structures of the urinary or reproductive tract such as the vagina or ureter, the lining mucosa of the lungs, or the epithelium forming the walls of the pericardium, pleurae or peritoneum.

In particular, the apparatus and methods of the invention are suitable for the culture of fibroblasts, keratinocytes and the production of stratified epidermis and/or full thickness skin.

Full thickness skin comprises epidermal and dermal layers. The epidermis is a stratified epithelium comprising keratinocytes. The dermis is a layer beneath the epidermis comprising fibroblasts and matrix components including collagen.

A challenging aspect of engineering full thickness skin in vitro is the production of stratified epidermal tissue. Stratification of the epidermis is crucial for skin function, and is required for the formation of a stratum corneum, the tissue layer that provides the barrier function of skin.

Current methods used to produce full thickness skin involve culturing keratinocytes and fibroblasts in rings set on de-epidermised dermis. Tissue medium must be changed on day 1 and the ring removed and transferred to an air liquid interface on day 2. Regular media changes are required, increasing the opportunity for contamination of the culture.

The apparatus and method of the invention provide for the engineering of full thickness skin comprising a dermis and stratified epidermal tissue. The invention provides for growth of full thickness skin on a suitable substrate while providing a gas permeable interface in contact with or in close proximity to the growing epidermis allowing gas exchange required for the differentiation of keratinocytes and stratification of the epidermis. It is not necessary to transfer the growing tissue to another culture vessel at any time, and few media changes or user interventions are required.

In various embodiments the apparatus and method of the invention further provide for full thickness skin comprising additional cells and tissues to improve the function of full thickness skin produced by methods of the invention after transplantation.

In one embodiment tissue comprising differentiated or stratified epithelium produced using a method or apparatus of the invention is further manipulated to form a structure. It is envisaged that any structure comprising an epithelial surface or lining may be formed. For example, tissue may be wrapped or folded to form a tubular structure, such as a vessel, urethra or oesophagus. Such methods are known in the art, for example, the methods described in Green et al., 2010. *Tissue Engineering* Vol 16, No 3, pages 1052-1064; Bhargava et al., 2004. *BJU International*, Vol 93: pages 807-811; and Bhargava et al., 2008. *European Urology*, Vol 53: pages 1263-1271), which are hereby incorporated by reference.

Structures comprising tissue produced using the methods or apparatus of the invention may be suitable for transplantation into a subject in need thereof.

In an alternative embodiment epithelial tissue produced by a method or using an apparatus of the invention is recovered from the apparatus and formed into the structure in situ during a surgical transplantation procedure. For example, in one embodiment tissue produced by a method or using an apparatus of the invention is formed into a urethra in situ during a urethroplasty procedure.

To reduce the opportunity for contamination, tissues produced using an apparatus of the invention according to the methods described herein may be transported in the apparatus from the laboratory to the operating theatre.

Treatment of Tissue Damage

The invention provides for the use of tissue, such as epithelium, epidermis, stratified epithelium, stratified epidermis and dermis, split thickness skin or full thickness skin, prepared using a method described herein for the treatment of tissue damage in subject in need thereof.

The invention further relates to a method of treating tissue damage in a subject in need thereof comprising the steps of
  a) providing an apparatus of the invention in which tissue, such as epithelium, stratified epithelium, epidermis, stratified epidermis, stratified epidermis and dermis, split thickness skin or full thickness skin, has been grown, for example in a method as herein described,
  b) recovering under sterile conditions the tissue from the apparatus, and
  c) applying the tissue to the patient.

In various embodiments the tissue damage is a wound, a chronic wound, a surgical wound, an ulcer, a non-healing wound, a scar, a surgical scar, a scald or a burn. In various embodiments the burn is a first degree burn, a second degree burn, a third degree burn, a deep dermal burn or a full thickness burn.

In various embodiments the tissue damage is epithelium located on a mucosal surface. In various embodiments the epithelium is located on or in skin, the lungs, the gastrointestinal tract (for example, the oesophagus or mouth), reproductive tract, or the urinary tract (for example, the urethra).

In a preferred embodiment the tissue is prepared using cells that are autologous to the subject. For example, in various embodiments the tissue is prepared using fibroblasts, keratinocytes, or fibroblasts and keratinocytes that are autologous to the subject. In an alternative embodiment the tissue is prepared using cells that are heterologous to the subject. In a further embodiment the tissue is prepared using cells that are autologous to the subject and cells that are heterologous to the subject.

It will be appreciated that cells autologous to the subject may be isolated using any method known in the art. For example, autologous cells may be isolated from a skin sample or skin biopsy taken from the subject by digesting the sample tissue and separating fibroblasts and/or keratinocytes from the digested tissue.

In one embodiment the tissue is an autograft, for example, a skin autograft. In various embodiments the tissue is an epidermal autograft, a split thickness skin autograft or a full thickness skin autograft. In another embodiment the tissue is an allogeneic graft.

It will be appreciated that the application of tissue prepared using cells autologous to the patient, such as an autograft, is highly desirable to reduce or prevent immune rejection of the tissue and to reduce the requirement for ongoing immunotherapy or another ancillary treatments.

In one embodiment the tissue comprises the tissue further comprises the substrate. In another embodiment the tissue is separated from the substrate before application to the patient.

Generally, the application of tissue to the patient will be by surgery. In one embodiment, recovery under sterile conditions is during or immediately prior to surgery, for example in the surgical suite.

Generally, the application of tissue to the patient will be at or adjacent the site of tissue damage. In various embodiments the tissues is applied to at least partially cover the site of tissue damage or to completely cover the site of tissue damage.

In one embodiment the tissue is applied to temporarily cover the site of tissue damage. In an alternative embodiment the tissue is applied to permanently cover the site of tissue damage.

In Vitro Testing

The efficacy and safety of topically applied pharmaceutical, nutraceutical or cosmetic products are typically tested using animal skin or live animals, human cadaver skin or synthetic human skin models.

Morphological differences between animal and human skin means that the excised animal skin or live animals for the testing of products is not optimal. Furthermore, there is considerable ethical concern about the use of live animals or animal skins for testing cosmetic products, including bans on such testing in some countries. For these reasons, there is a strong desire to identify alternatives to animal models for the testing of such products.

Inconsistent and highly variable results have been observed when human cadaver skin is used for product testing.

Cells or tissues prepared using the apparatus or methods described herein are useful for in vitro testing of pharmaceuticals, nutraceuticals or cosmetic products.

In various embodiments cells or tissue prepared using the apparatus or methods described herein are used to test transdermal penetration of a compound, to test the permeation of a compound across the epidermis, dermis or basement membrane, to test the efficacy of an active ingredient for treating or preventing a condition, for example, a skin condition, or to test the toxicity of a compound.

In various embodiments the cells or tissue are used to determine if a compound of interest is a skin irritant, for example, to determine if a compound of interest induces a skin rash, inflammation, or contact dermatitis.

In various embodiments the cells comprise fibroblasts, keratinocytes or immune cells, or a combination of any two or more thereof. In one embodiment the cells comprise fibroblasts and keratinocytes. In various embodiments the tissue is selected from the group comprising epidermis, stratified epidermis and dermis, stratified epidermis and dermis, split thickness skin or full thickness skin.

In various embodiments the compound is a pharmaceutical compound, a cosmetic compound or a nutraceutical compound.

In various embodiments the compound for testing is applied to tissue alone or in an admixture with pharmaceutically or cosmetically acceptable carriers, excipients or diluents.

In various embodiments the compound for testing is applied topically to the tissue in the form of a sterile cream, gel, pour-on or spot-on formulation, suspension, lotion, ointment, dusting powder, a drench, spray, drug-incorporated dressing, shampoo, collar or skin patch.

The invention consists in the foregoing and also envisages constructions of which the following gives examples only and in no way limit the scope thereof.

EXAMPLES

Example 1

This example outlines an investigation of the preparation of full thickness skin using an apparatus and method of the invention.
1. Method
  Sterilised substrate (Electrospun PLGA or any other dermal substitute compatible with skin cell growth) is attached to a stainless steel scaffold. The substrate is optionally coated with collagen IV (Collagen IV Sigma-Aldrich C5533, used at 10 ug/cm$^2$) for 2 hours then washed three times with phosphate buffered saline (PBS).

The scaffold with attached substrate is placed into a gas permeable interface (GPI) apparatus so that the collagen IV-coated side is facing towards the opening.

250 ml of Greens medium (DMEM:Hams F12 (Life Technologies 31765-035) 3:1, 10% FCS, 10 ng/ml EGF (Sigma-Aldrich E9644), 0.4 µg/ml hydrocortisone (Sigma-Aldrich H0396), 0.1 nM choleratoxin (Sigma-Aldrich C8052), 180 µM adenine (Sigma-Aldrich A2786), 5 ug/ml insulin (Sigma-Aldrich I9278), 5 µg/ml apotransferrin (Sigma-Aldrich T2036), 2 nM 3,3,5,-tri-idothyronine (Sigma-Aldrich T2752), 1× Penicillin/Streptomycin, 0.625 µg/ml Amphotercin B (Sigma-Aldrich A2942)) is added to the apparatus.

Fibroblasts and keratinocytes are detached from culture dishes and counted. 300,000 keratinocytes and 100,000 fibroblast per cm$^2$ are added into the GPI apparatus. The lid is placed on to seal the GPI apparatus. The apparatus is incubated at 37° C., 5% $CO_2$ for 48 hours.

The GPI apparatus is inverted, ensuring that the scaffold moves to the opposite end of the apparatus and the substrate is in direct contact with the gas permeable membrane. The apparatus is incubated at 37° C., 5% $CO_2$ for 14 days.

The GPI apparatus is opened, all liquid is discarded, and the scaffold is removed. A scalpel cut around the edges is used to release the skin from the scaffold.

2. Result

The method will produce full thickness skin comprising a dermis and stratified epidermis suitable for grafting on to a patient.

Example 2

This example outlines an investigation of the preparation of full thickness skin using an apparatus and method of the invention.
1. Method Sterilised substrate is attached as described for Example 1 to stainless steel scaffold. The substrate is optionally coated with collagen IV (Collagen IV Sigma-Aldrich C5533, used at 10 ug/cm$^2$) for 2 hours then washed three times with phosphate buffered saline (PBS).

The scaffold with attached substrate is placed into a gas permeable interface (GPI) apparatus so that the collagen IV coated side is facing away from the opening.

250 ml of Greens medium is added as described for Example 1.

100,000 fibroblasts per cm$^2$ are added into the GPI apparatus. The lid is placed on the GPI apparatus and sealed. The apparatus is incubated at 37° C., 5% $CO_2$ for at least 48 hours.

The GPI apparatus is inverted, ensuring that the scaffold moves to the opposite end of the apparatus.

300,000 keratinocytes per cm$^2$ are added into the GPI apparatus through the injection port such that the keratinocytes settle on the unseeded side of the substrate. The apparatus is incubated at 37° C., 5% $CO_2$ for 48 hours.

The GPI apparatus is inverted a second time, ensuring that the scaffold moves to the opposite end of the apparatus and the substrate is in direct contact with the gas permeable membrane. The apparatus is incubated at 37° C., 5% $CO_2$ for 14 days.

The GPI apparatus is opened, all liquid is discarded, and the scaffold is removed. A scalpel cut around the edges is used to release the skin from the scaffold.

2. Result

The method will produce full thickness skin comprising a dermis and stratified epidermis suitable for grafting on to a patient.

Example 3

This example outlines an investigation of the preparation of a stratified epidermis using an apparatus and method of the invention.
1. Method Sterilised substrate is attached as described for Example 1 to stainless steel scaffold. The substrate is optionally coated with collagen IV (Collagen IV Sigma-Aldrich C5533, used at 10 ug/cm$^2$) for 2 hours then washed three times with phosphate buffered saline (PBS).

The scaffold with attached substrate is placed into a gas permeable interface (GPI) apparatus so that the collagen IV coated side is facing towards the opening.

250 ml of Greens medium is added as described for Example 1.

300,000 keratinocytes per cm$^2$ are added into the GPI apparatus such that the keratinocytes settle on the unseeded side of the substrate. The lid is placed on the GPI apparatus and sealed. The apparatus is incubated at 37° C., 5% $CO_2$ for 48 hours.

The GPI apparatus is inverted ensuring that the scaffold moves to the opposite end of the apparatus and the substrate is in direct contact with the gas permeable membrane. The apparatus is incubated at 37° C., 5% $CO_2$ for 14 days.

The GPI apparatus is opened, all liquid is discarded, and the scaffold is removed. A scalpel cut around the edges is used to release the stratified epidermis from the scaffold.
2. Result The method will produce a stratified epidermis suitable for grafting on to a patient.

Example 4

This example compares skin prepared using a method of the invention utilising a gas permeable interface (GPI) with skin prepared using a prior art method utilising an air-liquid interface (ALI).
1. Preparation of Full Thickness Skin
Preparation of Adhered Cells De-epidermised acellular dermis (DED) was placed in a polystyrene tissue culture dish. A stainless steel ring with a 10 mm diameter aperture and 10 mm depth was set on DED and filled with Green's medium. 300,000 keratinocytes and 100,000 fibroblasts were added into the centre of the ring. The media was changed twice within 24 hours.
Preparation of Full Thickness Skin Using an Air-Liquid Interface (ALI)

Full thickness skin was prepared using a prior art method utilising an air-liquid interface as follows.

After 48 hours the ring was removed from the DED and the DED comprising adhered fibroblasts and keratinocytes transferred onto a stainless steel rack in a tissue culture dish comprising Greens medium. The rack consisted of a grid of holes, raised 7 mm off the base of the culture dish, through which medium can contact the DED. The level of medium in the culture dish was maintained such that the base of the DED, resting on the metal rack, was in contact with the medium and the top surface of the DED, upon which the keratinocytes and fibroblasts had been seeded, was exposed to air creating an air-liquid interface.

The cells were cultured for 14 days at the air-liquid interface with complete medium changes every two to three days.

Preparation of Full Thickness Skin Using a Gas Permeable Interface

Full thickness skin was prepared using a gas permeable interface (GPI) as follows.

After 48 hours the ring was removed from the DED and the DED transferred into an apparatus comprising a gas permeable membrane. The DED was placed in the device so that the adhered fibroblasts and keratinocytes were in contact with the gas permeable membrane located at the bottom of the apparatus.

The cells were cultured for 14 days at the gas permeable interface.

After 14 days tissue was harvested for analysis to assess the quality of the skin formed in contact with an air-liquid interface or with a gas permeable membrane.

2. Comparison of Full Thickness Skin

The skin produced using a GPI was of a similar thickness and appearance to the skin produced using the ALI.

Samples of each skin were stained with antibodies to: cytokeratin 19, a marker of keratinocyte stem cells; cytokeratin 14; a basal keratinocyte marker; and cytokeratin 10, a suprabasal keratinocyte marker; and examined by fluorescent microscopy. Five µm thick transverse sections of each frozen skin sample were fixed with acetone and blocked with a 0.25% casein solution. Primary antibodies against cytokeratin 10, cytokeratin 14, or cytokeratin 19 in Tris buffered saline (TBS) solution containing 1% foetal bovine serum (FBS) covered the sample sections. Samples were incubated for one hour at room temperature. Samples were washed once with TBS, then three times with rocking for five minutes each time. Secondary antibodies specific for each primary antibody with Alexa 488 dye conjugated, in TBS with 1% FBS containing nuclear stain 4',6-diamidino-2-phenylindole (DAPI), covered the sample sections. Samples were incubated for 30 minutes at room temperature. Samples were washed once with TBS, then twice with rocking for 15 minutes each time. Samples were covered with Prolong Gold mounting solution and a coverslip placed on top. Images were obtained for all samples of DAPI stain and each Alexa 488 stain using a fluorescent microscope.

Skin grown at the air-liquid interface (ALI) and skin grown at the gas permeable interface (GPI) demonstrated formation of a stratified epidermis.

Many layers of keratinocytes were present in both sample types. Changes in the shape of the nucleus of the keratinocytes in the epidermis, from round in the basal region, to flattened in the upper regions, indicated that a stratified epidermis had formed in skin grown at both the ALI and the GPI.

Skin grown at an ALI or GPI demonstrated expression of cytokeratin 10, a suprabasal keratinocyte marker, in the top layer of the epidermis indicating that a stratum corneum layer had been successfully formed, which in turn indicated that the keratinocyte differentiation and epidermal stratification process had been successfully completed.

Skin grown at an ALI or GPI showed expression of cytokeratin 14, a basal keratinocyte marker, in the layers of keratinocytes below the stratum corneum, indicating these keratinocytes were in a proliferative state, which is required for formation of a stratified epidermis. Skin grown at an ALI and GPI contained keratinocytes that stained positive for cytokeratin 19, a keratinocyte stem cell marker. The presence of keratinocyte stem cells indicates that all of the keratinocyte cell types required for continued renewal of the epidermis were present.

A comparison of skin produced at an ALI with skin grown at a GPI indicates that the GPI may result in a greater number of keratinocyte stem cells present in the epidermis, potentially producing a better stratified epidermis.

This example demonstrates that the method of the invention provides for preparation of full thickness skin having a stratified epidermis and similar features to skin produced using a prior art method.

Example 5

This example demonstrates the preparation of skin tissue using a method and apparatus of the invention.

Skin tissue prepared using (1) an apparatus described herein and (2) a prior art apparatus both utilising a GPI, was compared with skin tissue prepared using (3) a prior art method utilising an ALI.

1. Method

Electrospun PLGA was coated with collagen IV solution (10 ug/cm$^2$) for 2 hours at 37° C. to form the substrate. The coated PLGA was washed three times with phosphate buffered saline (PBS) before seeding fibroblasts and keratinocytes onto the coated surface. 100 cm$^2$ substrate was used for method (1), 6 cm$^2$ for method (2) and 1 cm$^2$ for method (3).

Method (1): Preparation of Skin Using a GPI Apparatus Described Herein

Collagen-coated electrospun PLGA was clamped into the scaffold of a GPI apparatus of the invention such that the coated side was flush with the top surface of the scaffold.

The scaffold was placed in the bottom of the GPI apparatus such that the coated side of the electrospun PLGA faced upwards.

The GPI apparatus was filled with 300 ml of Green's medium. The composition of Green's medium is described in Example 1.

13,000,000 keratinocytes and 2,500,000 fibroblasts were added to the GPI apparatus so that the keratinocytes and fibroblasts could attach to the coated electrospun PLGA.

The lid (comprising a GPI) was placed on the GPI apparatus and the GPI apparatus was sealed.

After 48 hours, the GPI apparatus was inverted to move the scaffold to the opposing end of the apparatus (the lid). In this position, the adhered fibroblasts and keratinocytes were in direct contact with the GPI in the lid.

The cells were cultured for 14 days and required no medium changes for that period of time.

After 14 days, skin tissue was harvested for analysis.

Method (2): Preparation of Skin Using a Prior Art GPI Apparatus

A stainless steel ring with a 25 mm diameter aperture and 10 mm depth was set on coated electrospun PLGA inside a 5 cm diameter culture dish and filled with Green's medium. 750,000 keratinocytes and 200,000 fibroblasts were added into the centre of the ring. The media was changed twice within 24 hours.

After 48 hours the ring was removed from the coated electrospun PLGA and the coated electrospun PLGA was transferred from the culture dish into a G-Rex10 apparatus (Wilson Wolf) with 20 mL of Green's medium, such that the adhered fibroblasts and keratinocytes were in contact with the GPI located at the bottom surface of the G-Rex10.

The cells were cultured for 14 days and required no medium changes for that period of time.

After 14 days, skin tissue was harvested for analysis.

Method (3): Preparation of Skin Using a ALI

A stainless steel ring with a 10 mm diameter aperture and 10 mm depth was set on coated electrospun PLGA inside a six well culture plate and filled with Green's medium.

130,000 keratinocytes and 34,000 fibroblasts were added into the centre of the ring. The media was changed twice within 24 hours.

After 48 hours the ring was removed from the coated electrospun PLGA and the coated electrospun PLGA comprising adhered fibroblasts and keratinocytes was transferred onto a stainless steel rack in a tissue culture dish comprising Green's medium. The rack consisted of a grid of holes, raised 7 mm off the base of the culture dish, through which medium can contact the coated electrospun PLGA. The level of medium in the culture dish was maintained such that the base of the coated electrospun PLGA, resting on the metal rack, was in contact with the medium and the top surface of the coated electrospun PLGA, upon which the keratinocytes and fibroblasts had been seeded, was exposed to air creating an air-liquid interface.

The cells were cultured for 14 days at the ALI with complete medium changes every two to three days.

After 14 days, skin tissue was harvested for analysis.

Analysis

Samples of each skin were stained with antibodies to pan-cytokeratin, a marker of all keratinocyte cells to assess epidermal quality, and vimentin, a marker of fibroblasts, to assess dermal quality, and examined by fluorescent microscopy.

Five μm thick transverse sections of each frozen skin sample were fixed with acetone and blocked with a 0.25% casein solution. Primary antibodies against pan-cytokeratin, or vimentin in Tris buffered saline (TBS) solution containing 1% foetal bovine serum (FBS) covered the sample sections. Samples were incubated for one hour at room temperature. Samples were washed once with TBS, then three times with rocking for five minutes each time. Secondary antibodies specific for each primary antibody with Alexa 488 dye conjugated, in TBS with 1% FBS containing nuclear stain 4',6-diamidino-2-phenylindole (DAPI), covered the sample sections. Samples were incubated for 30 minutes at room temperature. Samples were washed once with TBS, then twice with rocking for 15 minutes each time. Samples were covered with Prolong Gold mounting solution and a coverslip placed on top. Images were obtained for all samples of DAPI stain and each Alexa 488 stain using a fluorescent microscope.

2. Result

Methods (1), (2) and (3) all produced full thickness skin comprising a dermal layer with a stratified epidermis on top of the dermal layer. The dermal layer was the bottom layer of the skin produced, as evidenced by positive staining for the fibroblast marker Vimentin. The dermal layer was a single cell thick for skin tissue produced by all three methods.

A stratified epidermal layer formed above the dermal layer for skin tissue produced by all three methods. The epidermis comprised many layers of keratinocytes, as evidenced by positive staining for keratinocyte marker pan-cytokeratin. Stratification of the epidermis was observed in the pan-cytokeratin staining of skin samples from the layering of the cytokeratin. Keratinocytes in the basal layer were rounded, becoming flattened out in the intervening layers until a stratum corneum forms the top layer.

Stratification of the epidermis was also demonstrated by the morphology of the keratinocyte cell nuclei, shown by DAPI staining, in the layers of the epidermis. In the basal layers of the epidermis, keratinocyte cell nuclei were rounded, indicating healthy, basal keratinocytes capable of proliferation. Moving up through the epidermal layers the keratinocyte cell nuclei flatten out, indicating they have undergone the differentiation process required to achieve stratification. In the top layer where the keratinocyte cells have completed their differentiation process, the cell nuclei were either very thin or had disappeared completely producing a stratum corneum layer consisting of dead keratinocyte cells.

INDUSTRIAL APPLICATION

The apparatus and methods of the invention have utility for the engineering of many cells and tissues having a wide range of therapeutic, pharmaceutical, cosmeceutical, nutraceutical and other laboratory applications, including skin grafting and testing of pharmaceutical and cosmetic products.

The invention claimed is:

1. An apparatus for culturing cells or tissue, the apparatus comprising:
 a container comprising a first endwall, and at least one sidewall, a detachable second endwall adapted to engage with the container to define a chamber, and a movable scaffold disposed within the chamber, and a substrate on said scaffold;
 wherein at least a part of the first endwall comprises a gas permeable material;
 and wherein the apparatus is configurable between
 (a) a first mode in which the movable scaffold is in a position in which the substrate on the movable scaffold within the chamber is not disposed in gaseous communication with the gas permeable material, and
 (b) a second mode in which the movable scaffold is in a position in which the substrate on the movable scaffold within the chamber is disposed in gaseous communication with the gas permeable material;
 and wherein the apparatus includes an engagement means, extending through said at least one sidewall, for effecting movement of the scaffold between the first mode and the second mode;
 and wherein the chamber is liquidly sealable from the environment;
 and wherein the apparatus allows movement of the scaffold between
 i) a bottom of the chamber, defined by the gas permeable material of the first endwall, and
 ii) a top of the chamber, defined by a gas permeable material in the second endwall.

2. The apparatus according to claim 1, wherein the gas permeable material is polydimethylsiloxane.

3. The apparatus according to claim 1, wherein the substrate presents culturing surfaces on opposite planar sides of the substrate.

4. The apparatus according to claim 1, wherein the substrate is a biocompatible material.

5. The apparatus according to claim 1, wherein the substrate is gas permeable.

6. The apparatus according to claim 1, wherein the substrate is or comprises poly(lactic co-glycolic acid) (PLGA).

7. The apparatus according to claim 6, wherein the substrate is or comprises electrospun PLGA.

8. The apparatus according to claim 1, wherein the substrate comprises a surface treated to improve cell adhesion, cell migration, or tissue stratification.

9. The apparatus according to claim 1, wherein the scaffold comprises a first frame defining an interior perimeter and an exterior perimeter, said first frame comprising a substantially planar upper surface, a second frame defining an interior perimeter and an exterior perimeter, said second frame comprising a substantially planar upper surface, wherein the first frame and the second frame detachably engage around at least a part of their perimeters to define an interface to receive and hold a substrate, wherein when held the substrate is held in a substantially planar arrangement across the interior perimeter of the first frame, and wherein when engaged, the upper surface of the first frame and the upper surface of the second frame are substantially co-planar.

10. The apparatus according to claim 9, wherein the dimensions of the interior perimeter of the second frame at its upper surface are greater than the dimensions of the exterior perimeter of the first frame at its upper surface, such that the second frame engages around the exterior perimeter of the first frame at least the upper surface of the first frame.

11. A method for culturing stratified epidermal tissue or full thickness skin tissue, the method comprising the steps of: a) providing a suspension comprising keratinocytes and fibroblasts in an amount of tissue culture medium sufficient to support cell growth; b) introducing the suspension into the cell culture apparatus as defined in claim 1, c) incubating the cell culture apparatus containing the suspension for a time sufficient for at least some of the keratinocytes and/or fibroblasts to adhere to the substrate, d) adapting the cell culture apparatus to a second mode in which the substrate is and/or the cells are disposed in gaseous communication with the gas permeable membrane, and e) incubating the cell culture apparatus for a time sufficient to allow epidermal stratification to occur.

12. A The method according claim 11, comprising the following additional steps between steps d) and e):
 introducing a second suspension comprising cells to be cultured, and
 incubating the cell culture apparatus comprising the second suspension for a time sufficient for at least some of the cells in the second suspension to adhere to the substrate.

13. The apparatus of claim 1, wherein when the movable scaffold within the chamber is moved to be at or adjacent to and/or disposed in gaseous communication with the gas permeable material, the scaffold is in contact with the gas permeable material.

14. An apparatus for culturing cells or tissue, the apparatus comprising:
 a container comprising a first endwall, and at least one sidewall, a detachable second endwall adapted to engage with the container to define a chamber, a movable scaffold disposed within the chamber and on the scaffold a substrate for cells to reside upon;
 wherein at least a part of the first endwall comprises a gas permeable material;
 and wherein the apparatus is configurable between
  (a) a first mode in which the movable scaffold within the chamber is in a position in which the substrate thereon is not in gaseous communication with the gas permeable material, and
  (b) a second mode in which the movable scaffold within the chamber is in a position in which the substrate thereon is at or adjacent to and in gaseous communication with the gas permeable material;
 and wherein the apparatus includes an engagement means, extending through said at least one sidewall, for effecting movement of the scaffold between the first mode and the second mode;
 and wherein the chamber is liquidly sealable from the environment.

15. The apparatus according to claim 1, wherein the movement of the scaffold between the bottom of the chamber and the top of the chamber is substantially linear.

16. The apparatus according to claim 4, wherein the biocompatible material is biocompatible membrane.

* * * * *